United States Patent
Hoem et al.

(10) Patent No.: US 12,076,333 B2
(45) Date of Patent: *Sep. 3, 2024

(54) LYSOPHOSPHATIDYLCHOLINE COMPOSITIONS

(71) Applicant: AKER BIOMARINE HUMAN INGREDIENTS AS, Lysaker (NO)

(72) Inventors: Nils Hoem, Stamsund (NO); Finn Myhren, Stamsund (NO); Petter-Arnt Hals, Stamsund (NO); Armend Håti, Stamsund (NO)

(73) Assignee: AKER BIOMARINE HUMAN INGREDIENTS AS, Lysaker (NO)

( * ) Notice: Subject to any disclaimer, the term of this patent is extended or adjusted under 35 U.S.C. 154(b) by 248 days.

This patent is subject to a terminal disclaimer.

(21) Appl. No.: 17/370,703

(22) Filed: Jul. 8, 2021

(65) Prior Publication Data

US 2021/0338697 A1   Nov. 4, 2021

Related U.S. Application Data

(63) Continuation of application No. 16/229,031, filed on Dec. 21, 2018, now Pat. No. 11,065,267.

(60) Provisional application No. 62/608,891, filed on Dec. 21, 2017, provisional application No. 62/725,683, filed on Aug. 31, 2018.

(51) Int. Cl.
| | | |
|---|---|---|
| *A61K 31/685* | (2006.01) | |
| *A23D 9/00* | (2006.01) | |
| *A23J 7/00* | (2006.01) | |
| *A23L 33/115* | (2016.01) | |
| *A23L 33/12* | (2016.01) | |
| *A61K 31/202* | (2006.01) | |
| *C11B 1/02* | (2006.01) | |
| *C12P 13/00* | (2006.01) | |

(52) U.S. Cl.
CPC .............. *A61K 31/685* (2013.01); *A23D 9/00* (2013.01); *A23J 7/00* (2013.01); *A23L 33/115* (2016.08); *A61K 31/202* (2013.01); *C11B 1/025* (2013.01); *A23L 33/12* (2016.08); *A23V 2002/00* (2013.01); *C12P 13/001* (2013.01)

(58) Field of Classification Search
CPC ......... A23D 9/00; A23L 33/115; A23L 33/12; A23J 7/00; A23V 2002/00; A23V 2250/1846; A23V 2250/1882; A61K 31/202; A61K 31/685; C11B 1/025; C12P 13/001

See application file for complete search history.

(56) References Cited

U.S. PATENT DOCUMENTS

| | | |
|---|---|---|
| 4,849,137 A | 7/1989 | Kobayashi |
| 5,654,290 A | 8/1997 | Bayon et al. |
| 8,906,886 B2 | 12/2014 | Chen et al. |
| 9,290,781 B2 | 3/2016 | Yazawa et al. |
| 9,556,116 B2 | 1/2017 | Oroskar et al. |
| 9,560,333 B2 | 1/2017 | Takagi |
| 9,650,590 B2 | 5/2017 | Oroskar et al. |
| 10,117,882 B2 | 11/2018 | Bruheim et al. |
| 10,525,068 B2 | 1/2020 | Bruheim et al. |
| 2008/0021000 A1 | 1/2008 | Chen et al. |
| 2008/0044487 A1 | 2/2008 | Bruheim et al. |
| 2009/0281065 A1 | 11/2009 | Ramchand et al. |
| 2013/0281404 A1 | 10/2013 | Yazawa et al. |
| 2016/0345616 A1 | 12/2016 | Bruheim et al. |
| 2018/0161299 A1 | 6/2018 | Bortz |
| 2018/0325924 A1 | 11/2018 | Subbaiah |

FOREIGN PATENT DOCUMENTS

| | | |
|---|---|---|
| EP | 2085089 | 8/2009 |
| JP | 2017-209598 A | 11/2017 |
| WO | WO 2006/054183 | 5/2006 |
| WO | WO 2014/105576 | 7/2014 |
| WO | WO 2015/048554 | 4/2015 |
| WO | WO 2015/069097 | 5/2015 |
| WO | WO 2015/069108 | 5/2015 |
| WO | WO 2016/128830 | 8/2016 |
| WO | WO 2016/128838 | 8/2016 |
| WO | WO 2019/123015 | 6/2019 |

OTHER PUBLICATIONS

Tocher et. al., Biotechnology & Applied Biochemistry, vol. 8, pp. 83-95, publ. 1986 (Year: 1986).*
International Search Report and Written Opinion, International Patent Application No. PCT/IB2018/001588, mailed Apr. 26, 2019, 13 pages.
Bernoud et al. Preferential Transfer of 2-Docosahexaenoyl-1-Lysophophatidylcholine Through an In Vitro Blood-Brian Barrier Over Unesterfied Docosahexaenoic Acid, Journal of Neurochemistry, 72, 1999, 338-345.
Chen and Subbaiah Phospholipid and Fatty Acid Specificity of Endothelial Lipase: Potential Role of the Enzyme in the Delivery of Docosahexaenoic Acid (DHA) to Tissues, Biochim Biophys Acta. Oct. 2007; 1771(10): 1319-1328.
Chen et al. Plasma non-esterified docosahexaenoic acid is the major pool supplying the brain, Scientific Reports, Oct. 2015, 1-12.
Cho et al. Lipid and Fatty Acid Composition of the Antarctic Krill Euphausia superba, Ocean Research 21(2): 109-116, 1999.
Chouinard-Watkins et al. Mechanisms regulating brain docosahexaenoic acid uptake: what is the recent evidence? Curr Opin Clin Nutr Metab Care Mar. 2018, 21:71-77.
Chouinard-Watkins et al. Phospholipid class-specific brain enrichment in response to lysophosphatidylcholine docosahexaenoic acid infusion, BBA-Molecular and Cell Biology of Lipids 1862 (2017) 1092-1098.
Fourrier et al. Docosahexaenoic acid-containing choline phospholipid modulates LPS-induced neuroinflammation in vivo and in microglia in vitro, Journal of Neuroinflammation, 2017, 14:170, pp. 1-13.

(Continued)

*Primary Examiner* — Sarah Pihonak
(74) *Attorney, Agent, or Firm* — Casimir Jones, S.C.; J. Mitchell Jones

(57) ABSTRACT

The present invention provides marine lysophosphatidylcholine compositions for use in pharmaceuticals, nutraceuticals and functional foods, as well as methods for making marine lysophosphatidylcholine compositions.

17 Claims, 12 Drawing Sheets

(56) References Cited

OTHER PUBLICATIONS

Hachem et al. Efficient Docosahexaenoic Acid Uptake by the Brain from a Structured Phospholipid, Mol Neurobiol (2016) 53:3205-3215.
Hosomi et al. Effect of Dietary Partial Hydrolysate of Phospholipids, Rich in Docosahexaenoic Acid-Bound Lysophospholipids, on Lipid and Fatty Acid Composition in Rat Serum and Liver, Journal of Food Science, vol. 84, iss. 1, 2019, pp. 183-191.
Illingworth and Portman The Uptake and Metabolism of Plasma Lysophosphatidylcholine in vivo by the Brain and Squirrel Monkeys, Biochem. J. 1972 130, 557-567.
Kitson et al. Effect of dietary docosahexaenoic acid (DHA) in phospholipids or triglycerides on brain DHA uptake and accretion, Journal of Nutritional Biochemistry 33 (2016) 91-102.
Lacombe et al. Brain docosahexaenoic acid uptake and metabolism, Molecular Aspects of Medicine 64 (2018) 109-134.
Lagarde et al. Biological properties of a DHA-containing structured phospholipid (AceDoPC)to target the brain . . . Prostaglandins, Leukotrienes and Essential Fatty Acids, Elsevier, 2014, 92, pp. 63-66.
Li et al. Production of Structured Phosphatidylcholine with High Content of DHA/EPA by . . . Int. J. Mol. Sci. 2014, 15, 15244-15258.
Mnasri et al. Lipase-catalyzed production of lysophospholipids, OCL 2017, 24(4), D405, 1-6.
Nguyen et al. Mfsd2a is a transporter for the essential omega-3 fatty acid docosahexaenoic acid, Nature, May 2014, vol. 509, pp. 503-506.
Patrick, R.P. Role of phosphatidylcholine-DHA in preventing APOE4-associated Alzheimer's disease, The FASEB Journal, 33, 1554-1564, 2019.
Subbaiah Papasani V. et al. "Enhanced incorporation of dietary DHA into lymph phospholipids by altering its molecular carrier" Biochimica et Biophysica Acta-Molecular and Cell Biology of Lipids, vol. 1861, No. 8, May 10, 2016.
Sugasini et al. Dietary docosahexaenoic acid (DHA) as lysophosphatidylcholine, but not as free acid, enriches brain DHA and improves memory in adult mice, Nature Scientific Reports, Sep. 2017, 1-11.
Thies et al. Preferential incorporation of sn-2 lysoPC DHA over unesterfied DHA in the young rat brain, The American Physiological Society, 1994, pp. R1273-R1279.
Tsushima et al. Docosahexaenoic- and Eicosapentaenoic Acid-bound Lysophospholipids are More Effective in Suppressing Angiogenesis than Conjugated Docosahexaenoic Acid, J. Oleo Sci. 61, (8) 427-432 (2012).
Valenzuela et al. Supplementing female rats with DHA-lysophosphatidylcholine increases ocosahexaenoic acid and acetylcholine contents in the brain . . . , Grasas Y Aceites, 61 (1), ENERO-MARZO, 16-23, 2010.
Grupp et al., "Protection against Hypoxia-reoxygenation in the Absence of Poly (ADP-ribose) Synthetase in Isolated Working Hearts", J. Mol. Cell. Cardiol. (1999) 31: pp. 297-303.
Lagarde, M. et al. "Lysophosphatidylcholine as a Preferred Carrier Form of Docosahexaenoic Acid to the Brain" Journal of Molecular Neuroscience, vol. 16, 2001, 201-204.
Berge, K. et al. Krill oil supplementation lowers serum triglycerides without increasing low-density lipoprotein cholesterol in adults with borderline high or high triglyceride levels, Nutr Res. Feb. 2014;34(2):126-33.

\* cited by examiner

LYSOPHOSPHATIDYLCHOLINE COMPOSITIONS

CROSS-REFERENCE TO RELATED APPLICATIONS

This application is a continuation of U.S. patent application Ser. No. 16/229,031 filed Dec. 21, 2018, now allowed as U.S. Pat. No. 11,065,267, which claims the priority benefit of U.S. Provisional Application No. 62/725,683 filed Aug. 31, 2018, and U.S. Provisional Application No. 62/608,891, filed Dec. 21, 2017, which are incorporated herein by reference in their entireties.

FIELD OF THE INVENTION

The present invention provides marine lysophosphatidylcholine compositions for use in pharmaceuticals, nutraceuticals and functional foods, as well as methods for making marine lysophosphatidylcholine compositions.

BACKGROUND OF THE INVENTION

Lysophosphatidylcholine (LPC) is a compound resulting from partial hydrolysis of a phosphatidylcholine (PC) molecule so that one of the fatty acid groups attached to the PC molecule is removed.

Lysophosphatidylcholine, with one mole of fatty acid per mole of lipid in position sn-1, is found in trace amounts in most animal tissues (at greater concentrations, it disrupts membranes). It is produced by hydrolysis of dietary and biliary phosphatidylcholine and is absorbed as such in the intestines, but it is re-esterified before being exported in the lymph. In addition, it is formed in most tissues by hydrolysis of phosphatidylcholine by means of the superfamily of phospholipase A2 enzymes as part of the de-acylation/re-acylation cycle that controls the overall molecular species composition of the latter, as discussed above. In plasma of animal species, an appreciable amount of lysophosphatidylcholine is formed by the action of the enzyme lecithin: cholesterol acyltransferase (LCAT), which is secreted from the liver. This catalyses the transfer of fatty acids from position sn-2 of phosphatidylcholine to free cholesterol in plasma, with formation of cholesterol esters and of course of lysophosphatidylcholine, which consists of a mixture of molecular species with predominately saturated and mono- and dienoic fatty acid constituents. In plasma, it is bound to albumin and lipoproteins so that its effective concentration is reduced to a safe level. Identification of a highly specific phospholipase A2γ in peroxisomes that is unique in generating sn-2-arachidonoyl lysophosphatidylcholine suggests that this may be of relevance to eicosanoid generation and signalling. Elevated levels of 26:0-lysophosphatidylcholine in blood are reported to be characteristic of Zellweger spectrum disorders (the result of a defect in peroxisome biogenesis).

Lysophosphatidylcholine has pro-inflammatory properties and it is known to be a pathological component of oxidized lipoproteins (LDL) in plasma and of atherosclerotic lesions; for example, there is reportedly a specific enrichment of 2-arachidonoyl-lysophosphatidylcholine in carotid atheroma plaque from type 2 diabetic patients. Recently, it has been found to have some functions in cell signalling, and specific receptors (coupled to G proteins) have been identified. It activates the specific phospholipase C that releases diacylglycerols and inositol triphosphate with resultant increases in intracellular $Ca^{2+}$ and activation of protein kinase C. It also activates the mitogen-activated protein kinase in certain cell types, and it promotes demyelination in the nervous system. In vascular endothelial cells, it induces the important pro-inflammatory mediator cyclooxygenase-2 (COX-2), a key enzyme in prostaglandin synthesis. Elevated levels of lysophosphatidylcholine have been identified in cervical cancer and may be diagnostic for the disease. Some biological effects of lysophosphatidylcholine may be simply due to its ability to diffuse readily into membranes, altering their curvature and indirectly affecting the properties of membrane proteins.

WO2015048554 discloses methods for identifying compounds that modulate transport via the Mfsd2a protein and other potential uses of LPC compositions.

SUMMARY OF THE INVENTION

The present invention provides marine lysophosphatidylcholine compositions for use in pharmaceuticals, nutraceuticals and functional foods, as well as methods for making marine lysophosphatidylcholine compositions.

Accordingly, in some preferred embodiments, the present invention provides marine lysophosphatidylcholine (LPC) compositions or concentrates characterized in comprising from about 10% to about 100% LPC w/w of the composition and an omega-3 fatty acid content of from 5% to 50% w/w of the composition and optionally having one or more the following characteristics or properties: a) a 2-LPC:1-LPC ratio of from 1:8 to 18:1; b) a phosphatidylcholine (PC) content of less than 10% w/w of the composition; c) a phosphatidylethanolamine (PE) content of less than 1.2% w/w of the composition; d) a neutral lipid content of from 5% to 65% w/w of the composition; e) a 2-LPC ether content of less than 1.0% w/w; and f) a ratio of EPA:DHA of from 1:1 to 3:1 or a ratio of DHA:EPA of from 1:1 to 5:1.

In some preferred embodiments, the composition comprises from 60% to 100% LPC w/w of the composition. In some preferred embodiments, the composition comprises from 70% to 90% LPC w/w of the composition. In some preferred embodiments, the composition comprises from 20% to 50% LPC w/w of the composition. In some preferred embodiments, the composition comprises from 20% to 30% LPC w/w of the composition. In some preferred embodiments, the composition comprises from 10% to 20% LPC w/w of the composition.

In some preferred embodiments, the composition has an omega-3 fatty acid content of from 30% to 50% w/w of the composition. In some preferred embodiments, the composition has an omega-3 fatty acid content of from 35% to 45% w/w of the composition. In some preferred embodiments, the composition has an omega-3 fatty acid content of from 5% to 20% w/w of the composition.

In some preferred embodiments, the compositions have property (a). In some preferred embodiments, the compositions have property (b). In some preferred embodiments, the compositions have property (c). In some preferred embodiments, the compositions have property (d). In some preferred embodiments, the compositions have property (e). In some preferred embodiments, the compositions have property (f). In some preferred embodiments, the compositions have two or more of properties (a), (b) and (c). In some preferred embodiments, the compositions have two or more of properties (a), (b), (c), (d), (e) and (f). In some preferred embodiments, the compositions have three or more of properties (a), (b), (c), (d), (e) and (f). In some preferred embodiments, the compositions have four or more of properties (a), (b), (c), (d), (e) and (f). In some preferred embodiments, the compositions have five or more of properties (a), (b), (c), (d), (e) and (f). In some preferred embodiments, the compositions have properties (a), (b), (c), (d), (e) and (f).

In some preferred embodiments, the compositions are selected from the group consisting of a krill LPC composition, a herring LPC composition, a herring roe LPC composition, an algal LPC composition, and a *Calanus* LPC composition.

In some preferred embodiments, the present invention provides a pharmaceutical or nutraceutical composition comprising a composition as described above and a physiologically acceptable carrier. In some preferred embodiments, the physiologically acceptable carrier is a lipid carrier.

In some preferred embodiments, the present invention provides an oral delivery vehicle containing the marine LPC composition, pharmaceutical composition or nutraceutical composition as described above.

In some preferred embodiments, the present invention provides a lipid composition comprising a first lipid fraction and second lipid fraction, wherein the first lipid fraction is a marine LPC composition as described above and the second lipid fraction is obtained from a different source than the first lipid fraction and/or contains less than 20% LPC. In some preferred embodiments, the second lipid fraction is selected from the group consisting of a triglyceride fraction, a diglyceride fraction, a fatty acid ethyl ester fraction, a free fatty acid fraction and combinations thereof. In some preferred embodiments, the second lipid fraction is a marine lipid fraction comprising EPA and/or DHA. In some preferred embodiments, the present invention provides a pharmaceutical or nutraceutical composition comprising the lipid composition as just described and a physiologically acceptable carrier. In some preferred embodiments, the present invention provides an oral delivery vehicle containing the lipid composition as just described.

In some preferred embodiments, the present invention provides methods for making a lysophosphatidylcholine (LPC) composition with a high content of EPA and DHA from a marine raw material containing phospholipids comprising treating the marine raw material with a phospholipase that is not native to the marine raw material to provide a phospholipase treated raw material and fractionating the phospholipase treated raw material to provide a lipid composition having a higher lysophosphatidylcholine content than the starting raw material. In some preferred embodiments, the raw material is selected from the group consisting of a krill lipid preparation, a herring lipid preparation, a herring roe lipid preparation, an algal lipid preparation, and a *Calanus* lipid preparation. In some preferred embodiments, the krill lipid preparation is a *Euphausia superba* lipid preparation.

In some preferred embodiments, the raw material is contacted with a phospholipase in a solvent. In some preferred embodiments, the solvent is a mixture of water and an alcohol. In some preferred embodiments, the alcohol is ethanol. In some preferred embodiments, the raw material is contacted with a phospholipase in a mixture of about 85% water and 15% ethanol.

In some preferred embodiments, the enzyme is a phospholipase A1 (PLA1). In some preferred embodiments, the enzyme is a phospholipase A1 (PLA1), wherein the enzyme concentration is in the range of 0.1-20 vol/wt %, preferably 0.1-15 vol/wt %, more preferably 0.1-10 vol/wt %, further preferably 0.1-5 vol/wt %, most preferably 0.1-3 vol/wt %. In some preferred embodiments, the enzyme is a phospholipase A1 (PLA1), wherein the method is carried out at a pH of 3-12, preferably 4-10, more preferably 4-9, most preferably 5-9. In some preferred embodiments, the enzyme is a phospholipase A1 (PLA1), wherein the method is carried out between 4-95° C., preferably 4-85° C., more preferably 10-80° C., further preferably 15-70° C., even more preferably 15-65° C., most preferably 15-60° C.

In some preferred embodiments, the raw material has a content of EPA and DHA at the range of; EPA: 1-70 wt % and DHA: 1-70 wt %, more preferably EPA: 5-70 wt % and DHA: 5-70 wt %, most preferably EPA: 10-60 wt % and DHA: 10-60 wt %. In some preferred embodiments, the LPC composition has a content of EPA and DHA in the range of; EPA: 1-100 wt % and/or DHA: 1-100 wt %, more preferably EPA: 5-100 wt % and/or DHA: 5-100 wt %, most preferably EPA: 10-90 wt % and/or DHA: 10-90 wt %.

In some preferred embodiments, the LPC composition has an LPC content in the ranges of 10-100 wt %, preferably 20-100 wt %, more preferably 30-100 wt %, further preferably 40-100 wt %, most preferably 50-100 wt %. In some preferred embodiments, the LPC composition obtained by the process is characterized in comprising from about 20% to about 95% LPC w/w of the composition and an omega-3 fatty acid content of from 5% to 50% w/w of the composition and optionally having one or more of the following characteristics or properties: a) a 2-LPC:1-LPC ratio of from 1:8 to 18:1; b) a phosphatidylcholine (PC) content of less than 10% w/w of the composition; c) a phosphatidylethanolamine (PE) content of less than 1.2% w/w of the composition; d) a neutral lipid content of from 5% to 65% w/w of the composition; e) a 2-LPC ether content of less than 1.0% w/w; and f) a ratio of EPA:DHA of from 1:1 to 3:1 or a DHA:EPA ratio of 1:1 to 5:1.

In some preferred embodiments, the methods further comprise formulating the LPC composition for human consumption.

In some preferred embodiments, the present invention provides an LPC or lipid composition as described above, or made by a method as described above, for use to supplement the diet of a human subject, preferably of less than 10 years of age, more preferably less than 1 year of age, even more preferably less than 1 month of age, and most preferably a newborn.

In some preferred embodiments, the present invention provides marine lysophosphatidylcholine (LPC) compositions or concentrates characterized in comprising from about 60% to about 100% LPC w/w of the composition and an omega-3 fatty acid content of from 30% to 50% w/w of the composition and optionally having one or more the following characteristics or properties: a) a 2-LPC:1-LPC ratio of from 1:8 to 18:1 or more preferably from 1:1 to 10:1; b) a phosphatidylcholine (PC) content of less than 0.5% to 5% w/w of the composition; c) a phosphatidylethanolamine (PE) content of less than 0.5% w/w of the composition; d) a neutral lipid content of from less than 5% to 40% w/w of the composition; and e) a ratio 2-LPC:2-LPC ether of from 2.5:1 to 4:1.

In some preferred embodiments, the present invention provides marine lysophosphatidylcholine (LPC) compositions or concentrates characterized in comprising from about 10% to about 20% LPC w/w of the composition and an omega-3 fatty acid content of from 5% to 50% w/w of the composition and optionally having one or more the following characteristics or properties: a) a 2-LPC:1-LPC ratio of from 1:8 to 18:1 or more preferably from 1:1 to 10:1; b) a phosphatidylcholine (PC) content of less than 10% w/w of the composition; c) a phosphatidylethanolamine (PE) content of less than 1.2% w/w of the composition; d) a neutral lipid content of from 5% to 65% w/w of the composition; e) a 2-LPC ether content of less than 1.0% w/w; and f) a ratio of EPA:DHA of from 1:1 to 3:1 or a ratio of DHA:EPA of from 1:1 to 5:1.

In some preferred embodiments, the present invention provides marine lysophosphatidylcholine (LPC) compositions or concentrates characterized in comprising from about 20% to about 40% LPC w/w of the composition and an omega-3 fatty acid content of from 5% to 50% w/w of the composition and optionally having one or more the following characteristics or properties: a) a 2-LPC:1-LPC ratio of from 1:8 to 18:1 or more preferably from 1:1 to 10:1; b) a phosphatidylcholine (PC) content of less than 10% w/w of the composition; c) a phosphatidylethanolamine (PE) content of less than 1.2% w/w of the composition; d) a neutral lipid content of from 5% to 65% w/w of the composition; e) a 2-LPC ether content of less than 1.0% w/w; and f) a ratio of EPA:DHA of from 1:1 to 3:1 or a ratio of DHA:EPA of from 1:1 to 5:1.

In some preferred embodiments, the present invention provides marine lysophosphatidylcholine (LPC) compositions or concentrates characterized in comprising from about 40% to about 60% LPC w/w of the composition and an omega-3 fatty acid content of from 5% to 50% w/w of the composition and optionally having one or more the following characteristics or properties: a) a 2-LPC:1-LPC ratio of from 1:8 to 18:1 or more preferably from 1:1 to 10:1; b) a phosphatidylcholine (PC) content of less than 10% w/w of the composition; c) a phosphatidylethanolamine (PE) content of less than 1.2% w/w of the composition; d) a neutral lipid content of from 5% to 65% w/w of the composition; e) a 2-LPC ether content of less than 1.0% w/w; and f) a ratio of EPA:DHA of from 1:1 to 3:1 or a ratio of DHA:EPA of from 1:1 to 5:1.

In some preferred embodiments, the present invention provides marine lysophosphatidylcholine (LPC) compositions or concentrates characterized in comprising from about 60% to about 80% LPC w/w of the composition and an omega-3 fatty acid content of from 5% to 50% w/w of the composition and optionally having one or more the following characteristics or properties: a) a 2-LPC:1-LPC ratio of from 1:8 to 18:1 or more preferably from 1:1 to 10:1; b) a phosphatidylcholine (PC) content of less than 10% w/w of the composition; c) a phosphatidylethanolamine (PE) content of less than 1.2% w/w of the composition; d) a neutral lipid content of from 5% to 65% w/w of the composition; e) a 2-LPC ether content of less than 1.0% w/w; and f) a ratio of EPA:DHA of from 1:1 to 3:1 or a ratio of DHA:EPA of from 1:1 to 5:1.

In some preferred embodiments, the present invention provides marine lysophosphatidylcholine (LPC) compositions or concentrates characterized in comprising from about 60% to about 100% LPC w/w of the composition and an omega-3 fatty acid content of from 5% to 50% w/w of the composition and optionally having one or more the following characteristics or properties: a) a 2-LPC:1-LPC ratio of from 1:8 to 18:1 or more preferably from 1:1 to 10:1; b) a phosphatidylcholine (PC) content of less than 10% w/w of the composition; c) a phosphatidylethanolamine (PE) content of less than 1.2% w/w of the composition; d) a neutral lipid content of from 5% to 65% w/w of the composition; e) a 2-LPC ether content of less than 1.0% w/w; and f) a ratio of EPA:DHA of from 1:1 to 3:1 or a ratio of DHA:EPA of from 1:1 to 5:1.

In some embodiments, lysophospholipid compositions described above are provided for use in increasing the amount of EPA and/or DHA in a target tissue or organ by oral administration of the lysophospholipid composition. Preferred target tissues and organ according to the invention are adrenal gland, blood, bone, bone marrow, brain, fat (white), kidney (whole), large intestine mucosa, liver, lung, muscle, myocardium, pancreas, pituitary gland, prostate gland, skin, small intestine mucosa, spleen, stomach mucosa, testis, thymus, and/or thyroid gland. In some preferred embodiments, the increase of the amount in EPA and/or DHA is in comparison to an equivalent dose of EPA and/or DHA provided as a phospholipid (i.e., a phospholipid molecule comprising fatty acyl groups at both the SN-1 and SN-2 positions of the phospholipid.

DEFINITIONS

Figure 1:
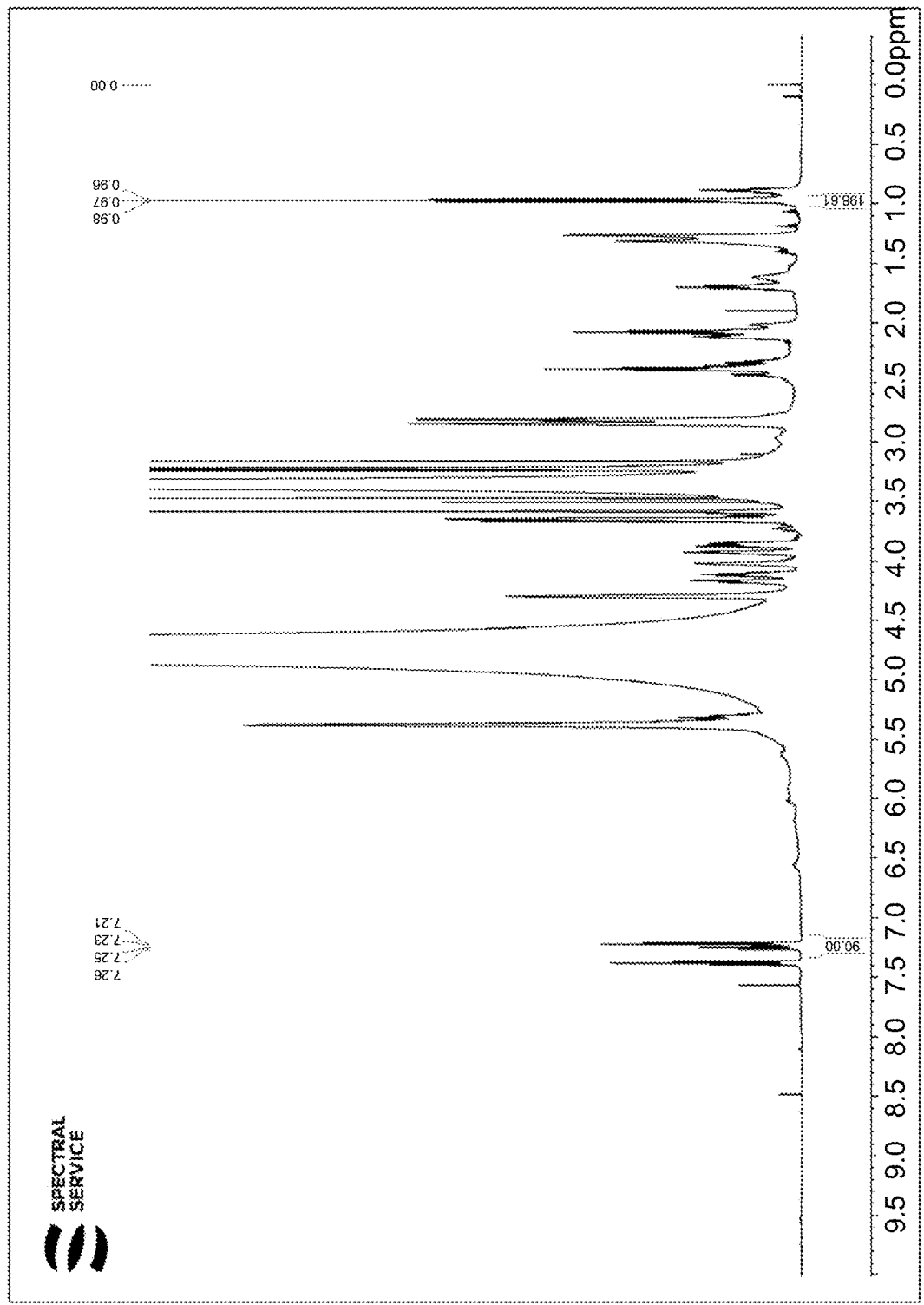
FIG. 1: $^1$H-NMR spectrum of sample AKB69444-1.

As used herein, "phospholipid" refers to an organic compound that has two fatty acid moieties attached at the sn-1 and sn-2 positions of glycerol and a head group linked by a phosphate residue at the sn-3 position of the glycerol. Exemplary headgroup moieties include choline, ethanolamine, serine and inositol. Phospholipids include phosphatidylcholine, phosphatidylserine, phosphatidylethanolamine, phosphatidylinositol and phosphatidic acid. The fatty acid moiety is the portion of the fatty acid molecule that is bound at the sn-1 or sn-2 position, for example by an ester or ether linkage. When the fatty acid moiety is a fatty acyl, the aliphatic chain of the fatty acyl is attached via an ester linkage and when the fatty acid moiety is an aliphatic chain of a fatty acid, the aliphatic chain is attached via an ether linkage. When a particular fatty acid is mentioned in connection with a phospholipid of the invention (e.g., EPA or DHA) it should therefore be taken as a reference to the relevant fatty acyl group or to its aliphatic chain.

As used herein, the term "ether phospholipid" refers to a phospholipid wherein the fatty acid moiety at one of the sn-1 or sn-2 positions is an aliphatic chain of a fatty acid attached via an ether linkage. Ether phospholipids include, for example, alkylacylphosphatidylcholine, alkylacylphosphatidylethanolamine and alkylacylphosphatidylserine.

As used herein, the term "lysophospholipid" refers to a phospholipid molecule that has a fatty acid moiety at one of the sn-1 and sn-2 positions of the molecule and an —OH group at the other position so that there is one mole of fatty acid moiety per mole of the phospholipid molecule. The term lysophosphatidylcholine (LPC) refers to a phosphatidylcholine molecule that has a fatty acid moiety at one of the sn-1 and sn-2 positions of the molecule and an —OH group at the other position so that there is one mole of fatty acid moiety per mole of lipid. Lysophospholipids may be may be designated as 1- or 2-lysophospholipids to denote the position of the —OH group in the molecule. Thus, 1-LPC refers to a lysophosphatidylcholine with an —OH group at the sn-1 position of the molecule and a fatty acid moiety at the sn-2 position. 2-LPC refers to a lysophosphatidylcholine with an —OH group at the sn-2 position of the molecule and a fatty acid moiety at the sn-1 position. When the lysophospholipid is an ether phospholipid, the fatty acid moiety is a fatty alcohol attached via an ether linkage at the sn-1 or sn-2 position. When the lysophospholipid is an ester phospholipid, the fatty acid moiety is a fatty acid ester attached via an ester linkage at the sn-1 or sn-2 position.

As used herein, the term "long chain polyunsaturated fatty acid" refers to a fatty acid having 20 or more carbons, and which is unsaturated at two or more bonds.

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexaenoic acid (DHA) and 7,10,13,16,19-docosapentaenoic acid (DPA).

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "functional food" refers to a food product to which a biologically active supplement has been added.

As used herein, the term "infant food" refers to a food product formulated for an infant such as formula.

As used herein, the term "elderly food" refers to a food product formulated for persons of advanced age.

As used herein, the term "pregnancy food" refers to a food product formulated for pregnant women.

As used herein, the term "nutritional supplement" refers to a food product formulated as a dietary or nutritional supplement to be used as part of a diet.

As used herein, the term w/w (weight/weight), unless otherwise specified, refers to the amount of a given substance in a composition on a weight basis and is expressed as a percentage of the total composition weight. For example, a composition comprising 50% w/w phospholipids means that the mass of the phospholipids is 50% of the total mass of the composition (i.e., 50 grams of phospholipids in 100 grams of the composition, such as an oil). When solvent concentration is designated throughout the specification, the concentration refers to the weight percent of solvent in the designated solvent solution. As a non-limiting example, 96% ethanol comprises 96% ethanol and 4% water. As another non-limiting example, when the specification describes a lipid solution as comprising 20% w/w dry matter and that the solvent is 95% ethanol, this means that 100 g of the solution comprises a total of 20 grams dry matter and 80 g of 95% ethanol.

As used herein, the term "krill meal" refers to dried powder prepared from krill and having a moisture content of from about 3% to about 15%.

DETAILED DESCRIPTION OF THE INVENTION

The present invention provides marine lysophosphatidylcholine compositions for use in pharmaceuticals, nutraceuticals and functional foods, as well as methods for making marine lysophosphatidylcholine (LPC) compositions. In particularly preferred embodiments, the LPC compositions are prepared from krill phospholipids, for example *Euphausia superba* or *Euphausia pacifica* phospholipids. In other preferred embodiments, the LPC compositions are prepared from *Calanus*, herring, herring roe, or algal phospholipids. Suitable krill crude phospholipid extracts, desalted krill phospholipid extracts and methods for processing krill are disclosed in PCT/IB2016/000208 and PCT/IB2016/000326, each of which is incorporated by reference herein in its entirety.

Intact phospholipids such as phosphatidylcholine are normally converted to lysophospholipids in the small intestine by the action of phospholipases. The lysophospholipids are then adsorbed into the body. Data presented herein demonstrate that when LPC compositions are administered orally in an animal model, that target omega-3 fatty acids in the composition are incorporated into a large number of tissues at both a faster rate and in a higher total amount than when orally administered in PC (phosphatidylcholine) compositions that do not contain appreciable amount of lysophospholipids. This result is surprising given the fact that one would expect there to be no difference because it is known the orally administered PC is converted in an efficient manner to lysophospholipids in the gut.

1. Starting Materials

The present invention is not limited to the use of any particular biological starting material. In preferred embodiments, a phospholipid extract is prepared from the biological starting material and the LPC compositions are made by enzymatic treatment of the phospholipid extract. The biological starting material may preferably be or be produced from an algal biomass, plant biomass or marine animal biomass. In preferred embodiments, marine animal biomasses are utilized as the starting material. Suitable marine animal biomasses include, but are not limited to krill, crabs, *Calanus*, plankton, eggs, crayfish, shrimp, fish, especially herring, and molluscs. The biological starting material can be either fresh or frozen, or can be a material produced from an algal, plant or marine animal biomass such as a meal, powder, hydrolysate, or coagulate (paste). The paste may be a wet paste or a dried paste. In some preferred embodiments, the biological starting material is a krill material, for example a krill meal, krill hydrolysate, krill coagulate, or fresh or frozen krill. Any species of krill may be utilized. In preferred embodiments, the krill is *Euphausia superba* or *Euphausia pacifica*.

In some particularly preferred embodiments, the biological starting material is a krill meal. Krill meal can be preferably be made by any standard marine meal process. In general, the krill meal is produced by cooking freshly caught krill at low temperature (approximately 80-85° C.) and drying to reduce the moisture content to approximately 5 to 8% and then grinding. In embodiments where the product is intended for human consumption, it is preferable to pack and store the meal under nitrogen without the addition of antioxidants.

Accordingly, the processes of the present invention may be used with a wide variety of starting materials. The remainder of the discussion of the processes generally refer to the use of krill meal as the starting material. However, it will be understood that any of the starting materials considered herein may be substituted for krill meal in the described processes.

2. Solvent Extraction from Krill Meal

In the first step of the extraction process, the krill meal is mixed with a suitable solvent to extract lipids from the meal. In contrast to prior art methods, the present invention utilizes conditions which preferably extract the maximum amount of lipids from the krill meal at the cost of an increased amount of contaminants in the initial solvent extract. In preferred embodiments, the solvent is an organic protic solvent, however other solvents known for use in extraction of food grade lipids may also be used such as acetone, hexane, etc. Suitable organic protic solvents include, but are not limited to, n-butanol, n-propanol, isopropanol, nitromethane, ethanol, and methanol. In particularly preferred embodiments, the protic solvent is ethanol.

In preferred embodiments, the concentration of the protic solvent used in the initial solvent extraction step is at least 90%, or preferably from about 94% to 98%, more preferably from about 95% to 97%, and is most preferably about 96% (e.g., 96% ethanol or methanol).

In some embodiments, the protic solvent is mixed with the biological starting material at a ratio of protic solvent:biological starting material of about 1:1 to 10:1, preferably about 3:1 to 6:1, more preferably about 4:1 to 5:1, and most preferably about 4.4:1.

In preferred embodiments, the biological starting material is extracted with protic solvent at a temperature of from about 5° C. to 65° C., from about 20° C. to about 60° C., preferably from about 30° C. to 50° C., more preferably from about 30° C. to 50° C., and most preferably at about 40° C. In some embodiments, the extraction time (i.e., the amount of time the biological starting material is in contact with the solvent) is from about 10 minutes to about 2 hours, preferably from about 15 minutes to 60 minutes, more preferably from about 20 minutes to about 45 minutes, and most preferably about 30 minutes.

Following the extraction step, a crude krill lipid solution containing the lipids from the krill meal is separated from the solvent/krill meal mixture, for example by decantation and or filtration. The insoluble material, comprising proteins and other useful materials is then dried to recover ethanol. The remaining protein-rich meal product may subsequently be used in food products, protein supplements, animal feeds and the like. In some embodiments, the decanted solution containing soluble lipids has a dry matter content of from about 4% to 9% w/w, preferably from about 5.5% to 7.5% w/w, and most preferably from about 6% to 7% w/w, where w/w refers to the weight of dry matter as a percent of the total solution weight. In preferred embodiments, the dry matter consists essentially of crude krill lipids, and preferably has a lipid content of greater than 90%, 95%, 96%, 97%, 98% or 99% w/w, wherein w/w refers to the weight of lipids a percent of the total dry matter weight.

3. Desalting and Concentration

In some embodiments, the crude krill lipid solution is desalted to remove hexane insoluble materials such as insoluble inorganic salts (e.g., NaCl with small or trace amounts of KCl and/or $AlCl_3$) as well as unwanted compounds such as trimethylamine oxide, and metals such as copper and arsenic. In some preferred embodiments, the LPC composition of the present invention is prepared from the desalted krill lipid composition. While the methods are described in reference to the desalted krill lipids described above, the methods are generally applicable any lipid fractions that contain phospholipids.

In some embodiments, the crude krill lipid solution is desalted by evaporating the solvent from crude krill lipid solution to provide a crude krill lipid composition and then subjecting the crude krill lipid composition to repeated washes with an aqueous solvent. Suitable aqueous solvents include, but are not limited to, ethanol blended with water or deionized water so that the ethanol concentration is from about 40% to 70%, preferably about 50% to 60%. In these embodiments, the crude krill lipid composition is mixed with the solvent, the lipid phase is recovered, and the aqueous phase is decanted. The washing step may be repeated as needed, for example 1, 2, 3, 4, 5 or more times. The ration of aqueous solvent:crude krill lipid composition is preferably from about 1:1 to 1:5 for each wash step, more preferably from about 1:1 to 2.5:1, and most preferably about 1:1.7.

In some embodiments, the crude lipid solution is desalted by chromatography. Suitable chromatographic media include silica gel media, including but not limited to spherical silica gels and derivatized silica gels such as C8 (octyl functionalized silica) and C18 (octadecyl functional silica) and ion exchange resins such as Dowex™ resins. In embodiments where chromatography is utilized, the crude krill lipids are preferably applied to the chromatographic medium in a protic solvent, preferably the same solvent used in the initial extraction (e.g., ethanol). Standard column chromatography methods may be utilized, however, moving bed chromatography or simulated moving bed chromatography apparatuses may preferably be utilized. The present invention is not limited to any particular type of chromatographic purification apparatus. Indeed, in preferred embodiments, the chromatographic purification apparatus may be a column, a fixed bed apparatus, a simulated moving bed apparatus or a moving bed apparatus. In some particularly preferred embodiments, the apparatus is a simulated moving bed (SMB) apparatus. Suitable SMB systems are disclosed, for example, in U.S. Pat. Nos. 9,556,116; 9,650,590; and 9,560,333; each of which is incorporated herein by reference in its entirety.

The composition of the desalted krill lipids on a dry matter basis may be preferably characterized as follows. In some embodiments, the desalted krill lipids preferably comprise from about 30% w/w to 50% w/w phospholipids, more preferably from about 35% w/w to about 45% w/w phospholipids, and most preferably about 40% w/w phospholipids, wherein w/w refers to the weight of the phospholipids as a percent of the total desalted kill lipid weight. In some embodiments, the desalted krill lipids preferably comprise from about 32% w/w to 52% w/w triglycerides, more preferably from about 36% w/w to about 48% w/w triglycerides, and most preferably about 42% w/w triglycerides, wherein w/w refers to the weight of the triglycerides as a percent of the total desalted krill lipid weight. In some embodiments, the desalted krill lipids preferably comprise from about 3% w/w to 13% w/w free fatty acids, more preferably from about 5% w/w to about 11% w/w free fatty acids, and most preferably about 8% w/w free fatty acids, wherein w/w refers to the weight of the free fatty acids as a percent of the total desalted krill lipid weight. In some embodiments, the desalted krill lipids preferably comprise from about 0.5% w/w to 5% w/w lysophospholipids, more preferably from about 0.8% w/w to about 3.2% w/w lysophospholipids, and most preferably about 1.2% to 2.8% w/w lysophospholipids, wherein w/w refers to the weight of the lysophospholipids as a percent of the total desalted krill lipid weight. In some embodiments, the desalted krill lipids preferably comprise less than about 1% w/w inorganic salts, more preferably less than about 0.5% w/w inorganic salts, even more preferably less than about 0.2% w/w w/w inorganic salts, and most preferably less than about 0.1% w/w inorganic salts, wherein w/w refers to the weight of the inorganic salts as a percent of the total desalted krill lipid weight. In some embodiments, the desalted krill lipids preferably comprise less than about 5 mg N/100 g, more preferably less than about 3 mg N/100 g, even more preferably less than about 2 mg N/100 g, and most preferably less than about 1 mg N/100 g, where the N content serves as a convenient proxy for trimethylamine oxide (TMAO) content. In some embodiments, the desalted krill lipids comprise less than about 10 ppm copper ($Cu^{++}$), more preferably less than about 5 ppm $Cu^{++}$, even more preferably less than about 2 ppm $Cu^{++}$, and most preferably less than about 1 ppm $Cu^{++}$. In some embodiments, the desalted krill lipids comprise less than about 10 ppm total arsenic ($As^{3+}$, organic and inorganic), more preferably less than about 5 ppm total arsenic, even more preferably less than about 3 ppm total arsenic, and most preferably less than about 1 ppm total arsenic. In some embodiments, the desalted krill lipids preferably comprise from about 0.01% to 2% w/w ethyl esters, more preferably from about 0.01% to about 1.5% w/w ethyl esters, and most preferably from about 0.01% to about 1% w/w ethyl esters, wherein w/w refers to the weight of the ethyl esters as a percent of the total desalted krill lipid weight. In some embodiments, the krill phospholipid compositions preferably comprise less than about 5%, 4%, 3% or 2% w/w ethyl esters down to a lower limit of 0.01% ethyl esters (i.e., between 5% and 0.01% w/w ethyl esters, between 4% and 0.01% w/w ethyl esters, between 3% and 0.01% w/w ethyl esters, or between 2% and 0.01% w/w ethyl esters), more preferably less than about 1.5% w/w ethyl esters, and most preferably less than about 1% w/w ethyl esters, wherein w/w refers to the weight of the ethyl esters as a percent of the total desalted krill lipid weight. In some embodiments, the desalted krill lipids have a conductivity of less than about 50 µS/cm when measured with 5% dry matter in 95% ethanol, more preferably a conductivity of less than about 30 µS/cm when measured with 5% dry matter in 95% ethanol, and most preferably a conductivity of less than about 20 µS/cm when measured with 5% dry matter in 95% ethanol. In some embodiments, the desalted krill lipids have a viscosity of from about 50 to 800 mPas at 25° C., more preferably from about 100 to 400 mPas at 25° C., and most preferably 180 to 340 mPas at 25° C. In some embodiments, the desalted krill lipid compositions have a pH of from about 6.7 to 8.3 when measured in 95% ethanol.

In some preferred embodiments, the LPC compositions of the present invention are prepared from a phospholipid composition made from the desalted krill lipid composition. While the methods are described in reference to the desalted krill lipids described above, the methods are generally applicable any lipid fractions that contain phospholipids.

Accordingly, in some embodiments, the dry matter content of a lipid composition containing phospholipids, such as the desalted krill lipid composition described above, is adjusted to a predetermined level by adding or removing solvent and the resulting mixture is allowed to fractionate so that the phospholipids are predominantly partitioned into one phase and the neutral lipids partitioned into a different phase. In some embodiments, a lipid composition containing phospholipids such as the desalted krill lipids is mixed with a suitable protic solvent, preferably ethanol, so that the dry matter (i.e., lipid) content of the resulting solution is from about 10% to 40% w/w, preferably about 15% to 35% w/w, more preferably about 18% to 30% w/w, and most preferably about 20% to 25% w/w. In embodiments where the desalting step already provides the lipids in a suitable protic alcohol solution, such as is the case where ethanol is used as the solvent for chromatography, the desalted krill lipid solution may preferably be evaporated to provide desired dry matter content, i.e., from about 10% to 40% w/w, preferably about 15% to 35% w/w, more preferably about 18% to 28% w/w, and most preferably about 20% to 22% w/w. Suitable methods for evaporation include, but are not limited to, evaporation under reduced pressure (e.g., vacuum distillation), falling film evaporation, and removal of solvents via a membrane.

Following adjustment of the dry matter content to the desired level by either adding or removing solvent, the solution is then allowed to fractionate into an upper, light phase solution with an enriched phospholipid content and a lower, heavy phase solution containing predominantly neutral lipids and a high level of astaxanthin. Preferably, the temperature of the solution during the fractionation step is controlled. In some embodiments, the temperature for the fractionation step is from about 0° C. to about 20° C., preferably from about 5° C. to about 15° C., more preferably from about 8° C. to about 12° C., and most preferably about 10° C.

In some embodiments, the concentration of the protic solvent may be varied in order to control the phospholipid concentration in the lipid composition of the upper phase. In some embodiments, the protic solvent has a concentration of from about 55% to 100%, more preferably about 65% to 98%. In some preferred embodiments, the protic solvent has a concentration of from about 90% to 100%, more preferably about 92% to 98%, and most preferably about 95%. In these embodiments, the phospholipid content on a dry matter basis of the lipids in the upper phase after fractionation is from about 50% to 70% w/w, preferably about 55% to 65% w/w and most preferably about 60% w/w. In still other preferred embodiments, the protic solvent has a concentration of from about 80% to 90% w/w, more preferably about 82% to 88% w/w, and most preferably about 85% w/w. In these embodiments, the phospholipid content on a dry matter basis of the lipids in the upper phase after fractionation is from about 70% to 90% w/w, preferably about 75% to 85% w/w and most preferably about 80% w/w.

In some embodiments, the upper and lower phases are separated by centrifugation, preferably cryocentrifugation with a two phase or three phase separator. In some embodiments, the centrifugation is conducted at from about 0° C. to about 30° C., more preferably from about 0° C. to about 10° C. and most preferably from about 3° C. to about 7° C. In general, the gravitational force utilized will depend on delta T between the phases. Lower temperatures provide a greater delta T. In some preferred embodiments, the G force employed in the separation is from about 8000×G to about 15000×G.

In some embodiments, the process steps of adjusting the dry matter content as described above through the centrifugation steps are repeated one or more times.

In some embodiments, the upper light phase is collected and processed further. The solvent is preferably removed from the upper phase by one or more evaporation steps to yield a krill phospholipid composition. The krill phospholipid compositions preferably comprise from about 50% to 85% w/w phospholipids, and more preferably from about 55% to 80% w/w phospholipids, wherein w/w refers to the weight of phospholipids as a percent of the total weight of the composition.

In some embodiments, the lower heavy phase is collected and processed further. In some embodiments, the solvent is removed from the lower phase to provide a krill neutral lipid composition. In some embodiments, the lower phase may be fractionated with protic solvent and subjected to a second centrifugation step to recover additional phospholipids not recovered in the first fractionation step. Again, the solvent is removed from the resulting lower phase to provide a krill neutral lipid composition. The krill neutral lipid composition in both instances in characterized in containing high levels of astaxanthin. In some embodiments, the krill neutral lipid composition may be combined or blended with the krill phospholipid composition to provide a lipid composition with desired levels of phospholipids, neutral lipids, and astaxanthin. In some embodiments, the krill neutral lipid composition may be further processed (e.g., by chromatography) to provide an astaxanthin composition. The astaxanthin composition may then be combined or blended with the krill phospholipid composition to provide a lipid composition with desired levels of phospholipids and astaxanthin.

In some embodiments, the processes further comprise the step of adding a triglyceride oil, such as medium chain triglyceride oil or long chain triglyceride oil, at any stage during the process. For example, the triglyceride oil may be added to the collected light phase, heavy phase, phospholipid composition or neutral lipid composition. In some embodiments, the process steps of adjusting the dry matter content as described above through the centrifugation steps and/or evaporation steps are repeated one or more times.

In some embodiments, krill phospholipid and neutral lipid compositions are produced by a further chromatography step. In these embodiments, at least a portion of the desalted lipid rich stream described above is introduced into to a polar liquid extraction zone comprising a fixed bed adsorber containing a macroporous styrenic polymeric bead type resin effective to adsorb neutral lipids. In preferred embodiments, the fixed bed chromatography step provides a polar lipid extract stream comprising solvent and at least 50 wt-% polar lipids on a dry basis. In some preferred embodiments, the fixed bed adsorber is intermittently regenerated with a hot ethanol stream at a hot regeneration temperature between about 40° C. and about 60° C. to provide a neutral lipid raffinate stream comprising solvent, neutral lipids and astaxanthin. In some embodiments, solvent is recovered polar lipid extract stream to provide a krill phospholipid composition and from the neutral lipid raffinate stream to provide a neutral lipid composition. These processes are described in more detail in co-pending U.S. application Ser. No. 14/619,102, which is incorporated herein by reference in its entirety.

In some embodiments, the krill phospholipid compositions on a dry matter basis preferably comprise from about 5% w/w to 35% w/w triglycerides, more preferably from about 10% w/w to about 30% w/w triglycerides, and most preferably about 15% to 25% w/w triglycerides, wherein w/w refers to the weight of the triglycerides as a percent of the total krill phospholipid composition weight. In some embodiments, the krill phospholipid compositions preferably comprise from about 2% w/w to 13% w/w free fatty acids, more preferably from about 4% w/w to about 11% w/w free fatty acids, and most preferably about 4% to 10% w/w free fatty acids, wherein w/w refers to the weight of the free fatty acids as a percent of the total krill phospholipid composition weight. In some embodiments, the krill phospholipid compositions preferably comprise from about 0.5% w/w to 10% w/w lysophospholipids, more preferably from about 0.8% w/w to about 7.0% w/w lysophospholipids, and most preferably less than about 5.0% w/w or 3.0% w/w lysophospholipids, wherein w/w refers to the weight of the lysophospholipids as a percent of the total krill phospholipid composition weight. In some embodiments, the krill phospholipid compositions preferably comprise less than about 1% w/w inorganic salts, more preferably less than about 0.5% w/w inorganic salts, even more preferably less than about 0.2% w/w inorganic salts, and most preferably less than about 0.1% or 0.05% w/w inorganic salts, wherein w/w refers to the weight of the inorganic salts as a percent of the total krill phospholipid composition weight. In some embodiments, the krill phospholipid composition preferably comprises less than about 5 mg N/100 g, more preferably less than about 3 mg N/100 g, even more preferably less than about 2 mg N/100 g, and most preferably less than about 1 mg N/100 g, where the N content serves as a convenient proxy for trimethylamine oxide (TMAO) content. In some embodiments, the krill phospholipid compositions comprise less than about 10 ppm copper ($Cu^{++}$), more preferably less than about 5 ppm $Cu^{++}$, even more preferably less than about 2 ppm $Cu^{++}$, and most preferably less than about 1 ppm $Cu^{++}$. In some embodiments, the krill phospholipid compositions comprise less than about 10 ppm total arsenic ($As^{3+}$), more preferably less than about 5 ppm total arsenic, even more preferably less than about 3 ppm total arsenic, and most preferably less than about 1 ppm total arsenic. In some embodiments, the krill phospholipid composition preferably comprise from about 0.01% to 2% w/w ethyl esters, more preferably from about 0.01% to about 1.5% w/w ethyl esters, and most preferably from about 0.01% to about 1% w/w ethyl esters, wherein w/w refers to the weight of the ethyl esters as a percent of the total krill phospholipid composition weight. In some embodiments, the krill phospholipid composition preferably comprise less than about 5%, 4%, 3% or 2% w/w ethyl esters down to a lower limit of 0.01% ethyl esters (i.e., between 5% and 0.01% w/w ethyl esters, between 4% and 0.01% w/w ethyl esters, between 3% and 0.01% w/w ethyl esters, or between 2% and 0.01% w/w ethyl esters), more preferably less than about 1.5% w/w ethyl esters, and most preferably less than about 1% w/w ethyl esters, wherein w/w refers to the weight of the ethyl esters as a percent of the total krill phospholipid composition weight. In some embodiments, the krill phospholipid composition have a conductivity of less than about 50 μS/cm when measured with 5% dry matter in 95% ethanol, more preferably a conductivity of less than about 30 μS/cm when measured with 5% dry matter in 95% ethanol, and most preferably a conductivity of less than about 20 μS/cm, 10 μS/cm, 5 μS/cm or 1 μS/cm when measured with 5% dry matter in 95% ethanol. In some embodiments, the krill phospholipid composition has a viscosity of from about 400 to 2000 mPas at 35° C., more preferably from about 500 to 1800 mPas at 35° C., and most preferably from about 600 to 1600 mPas at 35° C. In some embodiments, the krill phospholipid composition has a pH of from about 6.7 to 8.3 when measured in 95% ethanol.

4. Production of LPC Composition

In some preferred embodiments, the LPC compositions of the present invention are prepared from the phospholipid sources described above. In some preferred embodiments, the present invention provides methods for making a lysophosphatidylcholine (LPC) composition with a high content of EPA and DHA from a marine or other raw material containing phospholipids comprising treating the marine raw material with a phospholipase that is not native to the marine raw material to provide a phospholipase treated raw material and fractionating the phospholipase treated raw material to provide a lipid composition having a higher lysophosphatidylcholine content than the starting raw material. In some preferred embodiments, the raw material is selected from the group consisting of a krill lipid preparation, a herring lipid preparation, a herring roe lipid preparation, an algal lipid preparation, and a *Calanus* lipid preparation, thereby providing a krill LPC composition, a herring LPC composition, a herring roe LPC composition, an algal LPC composition, or a *Calanus* LPC composition. In some particularly preferred embodiments, the krill lipid preparation is a *Euphausia superba* lipid preparation. In some preferred embodiments, the raw material has a content of EPA and DHA at the range of; EPA: 1-70 wt % and DHA: 1-70 wt %, more preferably EPA: 5-70 wt % and DHA: 5-70 wt %, most preferably EPA: 10-60 wt % and DHA: 10-60 wt %.

In some embodiments, the raw material is contacted with a phospholipase in a solvent. The present invention is not limited to the use of any particular phospholipase. In some embodiments, the phospholipase is a phospholipase A1 (PLA1). In some particularly preferred embodiments, the enzyme is LECITASE™ Ultra, QUARA™ LowP. In some embodiments, the solvent is a mixture of water and an alcohol. In some preferred embodiments, the alcohol is ethanol. In still further preferred embodiments, the raw material is contacted with a phospholipase in a mixture of about 85% water and 15% ethanol. In some particularly preferred embodiments, the enzyme is a phospholipase A1 (PLA1), and the enzyme concentration is in the range of 0.1-20 vol/wt %, preferably 0.1-15 vol/wt %, more preferably 0.1-10 vol/wt %, further preferably 0.1-5 vol/wt %, most preferably 0.1-3 vol/wt %. In some preferred embodiments, the enzyme is a phospholipase A1 (PLA1), wherein the method is carried out at a pH of 3-12, preferably 4-10, more preferably 4-9, most preferably 5-9. In some preferred embodiments, the enzyme is a phospholipase A1 (PLA1), wherein the method is carried out between 4-95° C., preferably 4-85° C., more preferably 10-80° C., further preferably 15-70° C., even more preferably 15-65° C., most preferably 15-60° C.

In some preferred embodiments, the LPC compositions of the present invention are prepared by additional solvent concentration and/or chromatographic separation procedures. In some preferred embodiments, the enzyme-treated LPC composition is concentrated by phase separation in a polar/non-polar solvent system. In some preferred embodiments, the enzyme-treated LPC composition is mixed with a solvent system comprising equal amounts of a polar solvent (e.g., methanol) and a non-polar solvent (e.g., heptane). The resulting mixture is agitated, and the phases allowed to separate. The polar lipids (e.g., LPC and PC) partition into the polar phase. In some embodiments, the polar phase is removed, washed with heptane, and the polar phase is recovered. In some preferred embodiments, the polar phase is then evaporated to dryness to provide a concentrated LPC composition. In some embodiments, the LPC composition may be further concentrated by chromatographic procedures, for example, by flash chromatography using silica 60 gel followed by evaporation to dryness.

The methods described above produce LPC compositions with preferred characteristics and/or properties. In some preferred embodiments, the LPC composition has a content of EPA and DHA in the range of; EPA: 1-100 wt % and/or DHA: 1-100 wt %, more preferably EPA: 5-100 wt % and/or DHA: 5-100 wt %, most preferably EPA: 10-90 wt % and/or DHA: 10-90 wt %. In still further preferred embodiments, the LPC composition has an LPC content in the ranges of 10-100 wt %, preferably 20-100 wt %, more preferably 30-100 wt %, further preferably 40-100 wt %, most preferably 50-100 wt %.

In still other preferred embodiments, the LPC composition obtained by the process is characterized in comprising:
about 10% to about 100% LPC w/w of the composition, or from 60% to 100% LPC, from 70% to 90% LPC, from 20% to 50% LPC, from 20% to 40% LPC, from 20% to 30% LPC, 10% to 30% LPC and by having an omega-3 fatty acid content of from 5% to 60% w/w of the composition, from 5% to 50% w/w of the composition, from 5% to 40% of the composition or from 5% to 30% of the composition, or from 20% to 60% w/w of the composition, from 20% to 50% w/w of the composition, or from 20% to 40% w/w of the composition, or from 30% to 50% w/w of the composition. It will be recognized by those of skill in the art that the omega-3 fatty acid content includes the content of omega-3 fatty acid acyl chains that are linked by ester or ether bonds to phospholipid and glycerol molecules in the composition. The wt % of omega-s fatty acid acyl groups in the composition may preferably be determined by $^{1}$H-NMR or other suitable NMR techniques, including $^{13}$C-NMR. Alternatively, the omega-3 fatty acid content may be expressed in g/100 g of the fatty acids as analyzed by gas chromatography as is known in the art. In these embodiments, the lysophospholipid compositions preferably comprise from 10 to 50 g/100 g omega-3 fatty acids and most preferably from 20 to 40 g/100 g omega-3 fatty acids where g/100 grams is the weight of the omega-3 fatty acids per 100 grams of total fatty acids as measured by gas chromatography.

In preferred embodiments, the lysophospholipid compositions additionally have one or more the following characteristics or properties:

a) a 2-LPC:1-LPC ratio of from 1:8 to 18:1, and more preferably from 1.2:1 to 8:1, 1.2:1 to 4:1, 1.2:1 to 2:1, 4:1 to 10:1; or 5:1 to 12:1;

b) a phosphatidylcholine (PC) content of from 0.5% to 10% w/w of the composition, and more preferably less than 10%, 9%, 8%, 7%, 6% or 5% w/w of the composition;

c) a phosphatidylethanolamine (PE) content of less than 1.2%, 1.1%, 1.0%, 0.7% or 0.5% w/w of the composition;

d) a neutral lipid content of from about 5% to 65% w/w of the composition, or more preferably from about 45% to 65% w/w or 15% to 35% w/w;

e) a ratio of 2-LPC:2-LPC ether of from 15:1 to 50:1, and more preferably from 50:1 to 25:1 and wherein the compositions can preferably comprise less than 5%, 4%, 3%, 2%, 1.0%, 0.9%, 0.8%, 0.7%, 0.6%, 0.5%, 0.4%, 0.3%, 0.2% or 0.1% 2-LPC-ether; and/or f) a ratio of EPA:DHA of from 1:1 to 3:1 of DHA:EPA of from 1:1 to 5:1.

In some preferred embodiments, the compositions from comprise from 20% to 40% or from 23% to 35% LPC w/w of the composition. In some preferred embodiments, the compositions comprise from 40% to 60%, from 40% to 70%, or from 50% to 70% LPC w/w of the composition. In some preferred embodiments, the composition comprises from 70% to 90% LPC w/w of the composition. With regard to property (f), where the LPC composition is prepared from krill phospholipids, the LPC composition will preferably comprise a ratio of EPA:DHA of from 1:1 to 3:1 and more preferably from 1.5:1 to 2:5:1. With further regard to property (f), where the LPC composition is prepared from marine sources other than krill (e.g., herring, herring roe or marine algae), the LPC composition will preferably comprise a ratio of DHA:EPA of from 1:1 to 5:1, more preferably from 2:1 to 4:1, and most preferably from 2.5:1 to 3.5:1.

In some preferred embodiments, the composition has an omega-3 fatty acid content of from 35% to 45% w/w of the composition. In some preferred embodiments, the composition has property (a), (b), (c), (d), (e) or (f) or a combination the properties, for example: properties (a) and (b); (a) and (c); (a) and (d); (a) and (e); (a) and (f) (b) and (c); (b) and (d); (b) and (e); (b) and (f); (c) and (d); (c) and (e); ((c) and (f); (d) and (e); (d) and (f); (e) and (f); (a), (b) and (c); (a), (b) and (d); (a), (b) and (e); (a), (b) and (f); (a), (c) and (d); (a), (c) and (e); (a), (c) and (f); (a), (d) and (e); (a), (d) and (f); (b), (c) and (d); (b), (c) and (e); (b) (c) and) f); (b), (d) and (e); (b), (d) and (f); (c), (d) and (e); (c), (d) and (f); (a), (b), (c), and (d); (a), (b), (c), and (e); (a), (b), (c) and (f); (b), (c), (d), and (e); (b), (c), (d) and (f); (a), (c), (d), and (e); (a), (c), (d) and (f); (a), (b), (d), and (e); (a), (b), (d) and (f); (a), (b), (c), (d) and (e); (a), (b), (c), (d), and (f); (b), (c), (d), (e), and (f); (a), (b), (d), (e) and (f); (a), (b), (c), (e) and (f); and (a), (b), (c), (d), (e) and (f) as well as any other possible combinations. In some preferred embodiments, the compositions have two or more of properties (a), (b) and (c). In some preferred embodiments, the composition has two or more of properties (a), (b), (c), (d) and (e). In some preferred embodiments, the composition has three or more of properties (a), (b), (c), (d), (e) and (f). In some preferred embodiments, the composition has four or more of properties (a), (b), (c), (d) and (e). In some preferred embodiments, the composition has five or more of properties (a), (b), (c), (d), (e) and (f).

5. Formulation of LPC Compositions

In some preferred embodiments, the present invention provides a pharmaceutical or nutraceutical composition comprising an LPC composition as described above and a physiologically acceptable carrier. In some preferred embodiments, the physiologically acceptable carrier is a lipid carrier. In some preferred embodiments, the present invention provides an oral delivery vehicle containing a marine LPC composition, pharmaceutical composition or nutraceutical composition as described herein.

In some preferred embodiments, the present invention provides a lipid composition comprising a lipid fraction and second lipid fraction, wherein the first lipid fraction is the marine LPC composition as described herein and the second lipid fraction is obtained from a different source than the first lipid fraction and/or contains less than 20% LPC. In some preferred embodiments, the second lipid fraction is selected from the group consisting of a triglyceride fraction, a diglyceride fraction, a fatty acid ethyl ester fraction, a free fatty acid fraction and combinations thereof. In some preferred embodiments, the second lipid fraction is a marine lipid fraction comprising EPA and/or DHA. In some preferred embodiments, the present invention provides a pharmaceutical or nutraceutical composition comprising the lipid composition just described and a physiologically acceptable carrier. In some preferred embodiments, the present invention provides an oral delivery vehicle containing the lipid compositions just described.

The LPC compositions of the present invention are preferably administered orally. Accordingly, in some embodiments, the compositions of this invention (such as those described in the preceding sections) are contained in acceptable excipients and/or carriers for oral consumption. The actual form of the carrier, and thus, the composition itself, is not critical. The carrier may be a liquid, gel, gelcap, capsule, powder, solid tablet (coated or non-coated), tea, or the like. The composition is preferably in the form of a tablet or capsule and most preferably in the form of a soft gel capsule. Suitable excipient and/or carriers include vegetable oil, fish oil, krill oil, maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, PA).

In some embodiments, the LPC compositions are formulated for oral administration with flavoring agents or sweeteners. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate. Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. In addition to the carbohydrates described above, the nutritional supplement can contain natural or artificial (preferably low calorie) sweeteners, e.g., saccharides, cyclamates, aspartamine, aspartame, acesulfame K, and/or sorbitol.

The LPC compositions of the present invention may also be delivered as dietary supplements, nutritional supplements, or functional foods.

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandosterone (DHEA), green tea (polyphenols), inositol, kelp, dulse, bioflavonoids, maltodextrin, nettles, niacin, niacinamide, rosemary, selenium, silica (silicon dioxide, silica gel, horsetail, shavegrass, and the like), *Spirulina*, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising of the LPC compositions of the present invention. In preferred embodiments, the nutritional supplements comprise an effective amount of the components as described above. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

In still further embodiments, the present invention provides food products, prepared food products, or foodstuffs (i.e., functional foods) comprising the LPC compositions of the present invention. In preferred embodiments, the foods comprise an effective amount of the components as described above. For example, in some embodiments, beverages and solid or semi-solid foods comprising the fatty acids or derivatives thereof are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour).

In some preferred embodiments, the LPC compositions are incorporated into chewable matrices. Preferred chewable matrices jelly candies and gelatin-based gummi candy. Exemplary gummi candies include gummi bears, gummi worms, gummi frogs, gummi hamburgers, gummi cherries, gummi soda bottles, gummi sharks, gummi army men, gummi hippopotami, gummi lobsters, gummi watermelons, gummi octopuses, gummi apples, gummi peaches, and gummi oranges. The terms "gummi" and "gummy" are used interchangeably herein.

In some embodiments, the present invention provides compositions comprising the LPC compositions described above and one or more additional omega-3 fatty acid derivatives or free fatty acids. The omega-3 fatty acid derivatives or free fatty acids may be derived from the neutral lipid extract or from an additional source, such as fish oil or omega-3 ester composition. In some embodiments, the one or more additional omega-3 fatty acid derivatives are selected from omega-3 esters and glycerides. For example, in some embodiments, the composition may comprise from about 1% to about 60% w/w of the krill oil composition (i.e., weight of phospholipid compounds/total weight of composition), with the remaining 99% to 40% w/w of the composition being omega-3 glycerides, esters, or free fatty acids or a combination thereof (i.e., weight of omega-3 glycerides, esters, or free fatty acids or a combination thereof/total weight of the composition). In some embodiments, the composition may comprise from about 5% to about 60% w/w phospholipids, with the remaining 95% to 40% w/w of the composition being omega-3 glycerides, esters, or free fatty acids or a combination thereof. In some embodiments, the composition may comprise from about 20% to about 60% w/w phospholipids, with the remaining 80% to 40% w/w of the composition being omega-3 glycerides, esters, or free fatty acids or a combination thereof. In some embodiments, the composition may comprise from about 30% to about 60% w/w phospholipids, with the remaining 70% to 40% w/w of the composition being omega-3 glycerides, esters, or free fatty acids or a combination thereof. In some embodiments, the composition may comprise from about 40% to about 60% w/w phospholipids, with the remaining 60% to 40% w/w of the composition being omega-3 glycerides, esters, or free fatty acids or a combination thereof. In some embodiments, the composition may comprise from about 50% to about 60% w/w phospholipids, with the remaining 50% to 40% w/w of the composition being omega-3 glycerides, esters, or free fatty acids or a combination thereof.

The LPC compositions of the present invention may further be incorporated into animal and fish feeds and rations. Many different feed rations may be formulated for animals and fish from many different feed ingredients. Rations are generally formulated to provide nutrients in accordance with National Research Council standards. The feedstuffs used in the ration are chosen according to market price and availability. Thus, some components of the ration may change over time. In the feeds of the present invention, the ration will always contain an LPC composition of the invention, preferably in an amount of from 0.1% to 50%, 0.5% to 50%, 1.0% to 40%, 1.0% to 30%, 1.0% to 20%, 1.0% to 10%, 0.1% to 10%, or 0.5% to 5% of the total fat in the ration. For discussions on feed ration formulation, actual rations and NRC guidelines, see Church, Livestock Feeds and Feeding, O&B Books, Inc., Corvallis, Oreg. (1984) and Feeds and Nutrition Digest, Ensminger, Oldfield and Heineman eds., Ensminger Publishing Corporation, Clovis, Calif. (1990), incorporated herein by reference.

The animal feed rations of the present invention may be characterized according to NRC requirements. NRC requirements may be found in Church, Livestock Feeds and Feeding, O&B Books, Inc., Corvallis, Oreg. (1984), or other nutritional standards. Animal and fish rations are traditionally balanced using the protein and energy requirements, and then adjusted if needed to meet the other requirements. The animal and fish feeds of the present invention will contain about 0.05% to 5% lipids plus other feed materials necessary to balance the feed to meet the NRC requirements (or other recognized requirements) for the different stages of growth and maintenance.

The relative amounts of protein and energy are adjusted to reflect standard requirements. The amounts of feed components will vary with the stage of animal fed. A growing ration for young animals and fish will have higher protein levels, while a finishing ration for finishing animals for market will have higher energy values which are supplied by carbohydrates. For example, prestarter, starter and grower-finisher rations for various animals will generally contain about 20-24% protein, 18-20% protein and 13-17% protein respectively. In some feeding situations, care must be taken to provide the appropriate amino acids as well as overall protein content. Energy requirements may also be met by addition of fat to the ration. In the present invention, the lysophospholipid composition provides part of the energy requirement.

Typical salmon rations of the invention comprise from about 5% to 65% fish meal and/or krill meal, 5% to 30% vegetable oil and 5%-15% fish oil, expressed as % weight of component/weight of the ration (% w/w) and from 0.5% to 5% of an LPC composition of the present invention to provide a total fat content of from 10% to 45% w/w of the ration. In some embodiments, the rations have a crude protein content of from about 32% to 46%, preferably from about 36% to 42%, a crude lipid content of from about 26% to 42%, preferably from about 28% to 38%, a carbohydrate (NFE) content of from about 11% to 18%, preferably from about 13% to 15%, a fiber content of from about 1% to 5%, preferably from about 1.5% to 2.5%, an ash content of from about 4% to 7%, preferably about 4.5% to 6.5%, a total phosphorus content (P) of from about 0.5% to 1.1%, preferably about 0.6% to 1.0%, a gross energy content of from about 20 to 30 MJ/kg, preferably from about 23 to 28 MJ/kg, and a digestible energy content of from about 20 to 24 MJ/kg.

Other ingredients may be added to the feed ration. These ingredients include, but are not limited to, mineral supplements such as calcium, phosphorus, salt, selenium and zinc; vitamin supplements such as Vitamins A, B, D, E, and K; amino acid supplements such as lysine; coccidiostats, except in hog feeds, or growth promoters such as bacitracin or virginamycin; and other active drugs such as chlortetracycline, sulfathiozole, and penicillin. For vitamin, mineral and antibiotic supplement formulation see Church, Livestock Feeds and Feeding, O&B Books, Inc., Corvallis, Oreg. (1984).

In a preferred embodiment, the lysophospholipid compositions are incorporated into a pelleted feed for administration to domestic animals. Pelleted feed is created by first mixing feed components and then compacting and extruding the feed components through a die with heat and pressure. The feed is pelleted by methods known in the art, which are described in MacBain, Pelleting Animal Feed, American Feed Manufacturers Association, Arlington, Va. (1974), incorporated herein by reference. When incorporating added fat into pelleted feed, caution is needed in order to avoid making mealy pellets. Generally, only about 2% of the fat is added during pelleting, with the rest added after the pellets have cooled.

The oil and the feed containing the oil may be stabilized by the addition of antioxidants. Therefore, antioxidants may be added as chemical preservatives in accordance with F.D.A. regulations as listed in the 1997 Official Publication, Association of Feed Control Officials Incorporated (1997), herein incorporated by reference. Suitable antioxidants include, but are not limited to: Lecithin, tocopherols, ascorbate, ascorbyl palmitate and spice extracts such as rosemary extract.

The feeds are formulated as above, and tailored to the requirements of the animal to be fed in accordance with NRC guidelines. For example, feeds may be formulated for dogs, cats, poultry, cattle, shrimp, and fish such as salmon, trout, catfish and tilapia. Various feed formulations, balancing methods and requirements for these animals are discussed in Church, Livestock Feeds and Feeding, O&B Books, Inc., Corvallis, Oreg. (1984) and Feeds and Nutrition Digest, Ensminger, Oldfield and Heineman eds., Ensminger Publishing Corporation, Clovis, Calif. (1990), incorporated herein by reference.

6. Uses of Krill Phospholipid Compositions

In some embodiments, lysophospholipid compositions of the present invention are provided for use in increasing the amount of EPA and/or DHA in a target tissue or organ by oral administration of the lysophospholipid composition. Preferred target tissues and organ according to the invention are adrenal gland, blood, bone, bone marrow, brain, fat (white), kidney (whole), large intestine mucosa, liver, lung, muscle, myocardium, pancreas, pituitary gland, prostate gland, skin, small intestine mucosa, spleen, stomach mucosa, testis, thymus, and/or thyroid gland.

In some embodiments, an effective amount of the compounds or compositions described above are administered to a subject in need thereof to treat, prevent, or improve cognition and/or a cognitive disease, disorder or impairment (memory, concentration, learning (deficit)), or to treat or prevent neurodegenerative disorders. In some embodiments, the cognitive disease, disorder or impairment is selected from Attention Deficit Disorder (ADD), Attention Deficit Hyperactivity Disorder (ADHD), autism/autism spectrum disorder (ASD), (dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson disease, Lou Gehrig's disease, pre-dementia syndrome, Lewy body dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well-being, neurodevelopmental, neurodegenerative disorders, hormonal disorders, neurological imbalance or any combinations thereof. In a specific embodiment, the cognitive disorder is memory impairment.

In some embodiments, an effective amount of the compounds or compositions described above are administered to a subject in need thereof to treat or prevent a cardiovascular disorder or metabolic syndrome. In some embodiments, the cardiovascular disorder is selected from atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, acute coronary syndrome (ACS), non-alcoholic fatty liver disease/non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel and diabetic autonomic neuropathy.

In some embodiments, an effective amount of the compounds or compositions described above are administered to a subject in need thereof to inhibit, prevent, or treat inflammation or an inflammatory disease. In some embodiments, the inflammation or inflammatory disease is selected from organ transplant rejection; reoxygenation injury resulting from organ transplantation (see Grupp et al., J. Mol. Cell. Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, Epilepsy, amyotrophic lateral sclerosis and viral or autoimmune encephalitis, preeclampsia; chronic liver failure, brain and spinal cord trauma, and cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also, inflammation that results from surgery and trauma can be treated with the phospholipid compositions.

In some embodiments, the LPC compositions described above are administered to a subject in need thereof to treat a disease or condition associated with red blood cells and cell membranes, and in particular a disease or conditions associated with an abnormality in red blood cells of cell membranes. In some embodiments, the condition or disease is sickle cell disease, sickle cell anemia, or sickle cell trait. In some embodiments, the condition or disease is thalassemia (alpha-, beta- or delta-), thalassemia in combination with a hemoglobinopathy (Hemoglobin E, Hemoglobin S, or Hemoglobin C), splenomegaly, or membrane abnormalities such as acanthocytes or spur/spike cells, codocytes (target cells), echinocytes (burr cells), elliptocytes and ovalocytes, spherocytes, stomatocytes (mouth cells) and degmacytes ("bite cells").

In some embodiments, the effective amount comprises from about 0.1 to about 5 grams of the krill phospholipid composition, preferably from about 0.2 to about 3 grams of the krill phospholipid composition, and most preferably about 0.5 to about 1.5 grams of the krill phospholipid composition.

The krill lysophospholipid compositions of the present invention may be used to treat a variety of subjects. Suitable subjects include humans as well as domestic animals (such as cattle, horses, sheep, pigs, goats, fish and shrimp), non-human primates, and companion animals (such as dogs, cats and birds). In some preferred embodiments, the subject is a human subject of less than 10 years of age, more preferably less than 1 year of age, even more preferably less than 1 month of age, and most preferably a newborn. In some preferred embodiments, the human subject is from about 10 to 20 years of age. In some preferred embodiments, the human subject is from about 20 to 50 years of age. In some preferred embodiments, the human subject is from about 50 to 100 years of age. In some preferred embodiments, the human subject is from about 60 to 100 years of age. In some preferred embodiments, the human subject is from about 70 to 100 years of age.

EXPERIMENTAL

Example 1—SUPERBA™ BOOST™

This example describes the production of a LPC composition using SUPERBA™ BOOST® (Aker Biomarine AS, Lysaker, NO) as the starting phospholipid source. The SUPERBA™ BOOST™ is preferably produced by the SMB processes described elsewhere herein. SUPERBA™ BOOST™ is a krill phospholipid composition wherein 1000 mg contains 560 mg phospholipids, 150 mg EPA and 70 mg DHA. Briefly, 9 grams of SUPERBA™ BOOST™ is mixed into 90 ml EtOH and then 450 ml water is added in one liter round bottom reaction flask purged with nitrogen. Next, 0.40 ml LECITASE™ Ultra is added and the reaction is allowed to proceed for 30 minutes with stirring. 500 ml EtOH is then added to deactivate the enzyme and the mixture is evaporated to dryness using a rotovap. Next, a solvent-based separation is performed. The enzyme-treated krill lipid sample is mixed with a solvent bath with heptane and methanol. The LPC and PC species migrate into the polar solvent (methanol) and the nonpolar lipids partition into the heptane. Decanting the heptane phase leaves a polar phase with high amount of polar lipids including LPC and PC. 250 ml each heptane and MeOH are added to the dried lipid composition in a flask. The flask is shaken vigorously, and the phases allowed to separate. The upper nonpolar heptane phase is decanted and another 250 ml heptane is added to the polar MeOH phase and the separation repeated. 10 grams silica gel is then added to the MeOH extract and the solution is evaporated to dryness in a rotovap. The LPC is then purified from the dried lipid composition by flash chromatography (100 g Silica gel in a 5 cm diameter column). The LPC is eluted with a series of mobile phases: MPA (heptane); MPB (Toluene:Methanol:Triethylamine, 60:40:1); and Methanol:Triethylamine, 95:5). The fractions are collected and evaporated to dryness.

Figure 2:
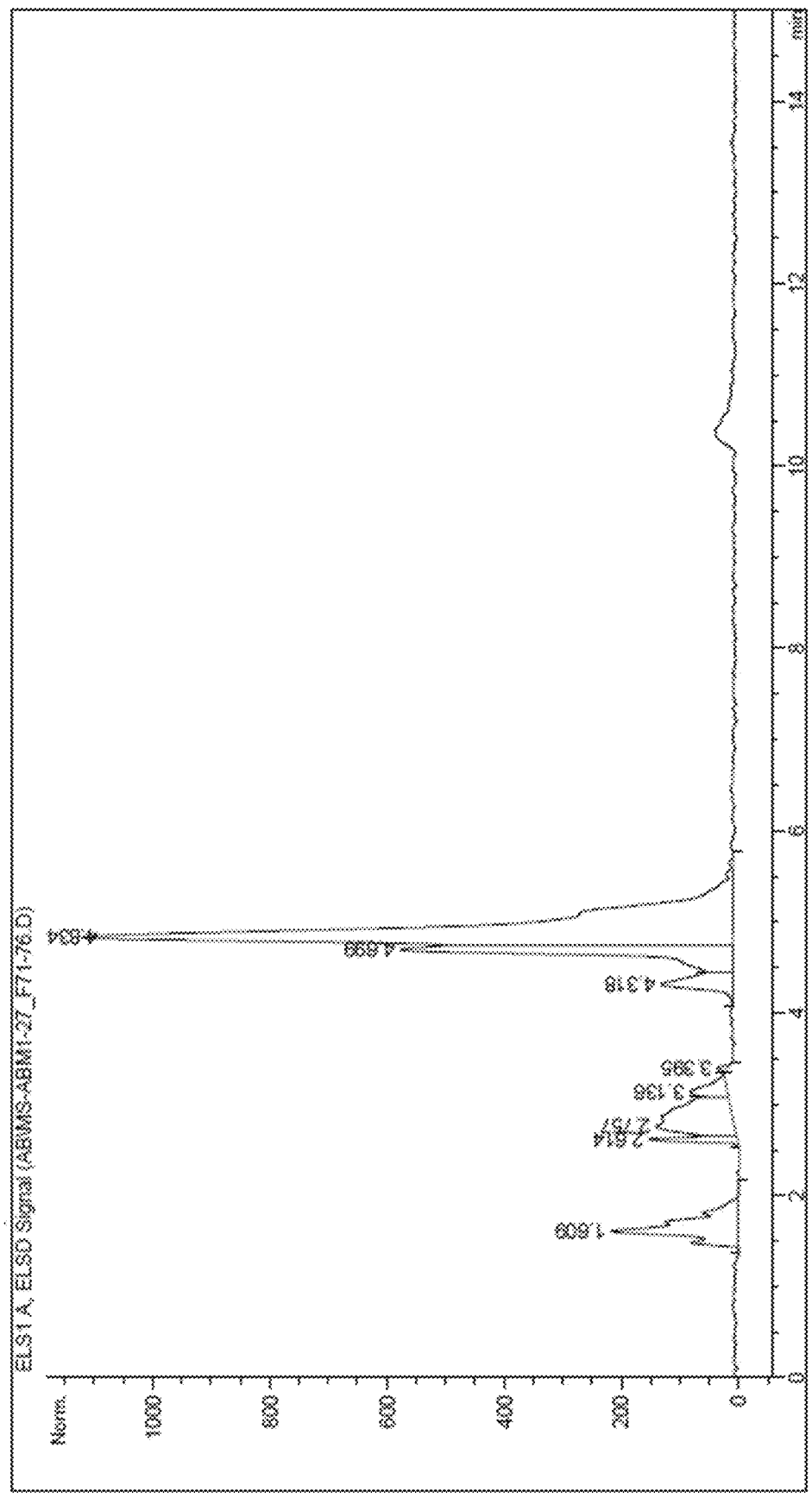
FIG. 2: HPLC chromatogram of LPC product, sample AKB69444-1.
Figure 3:
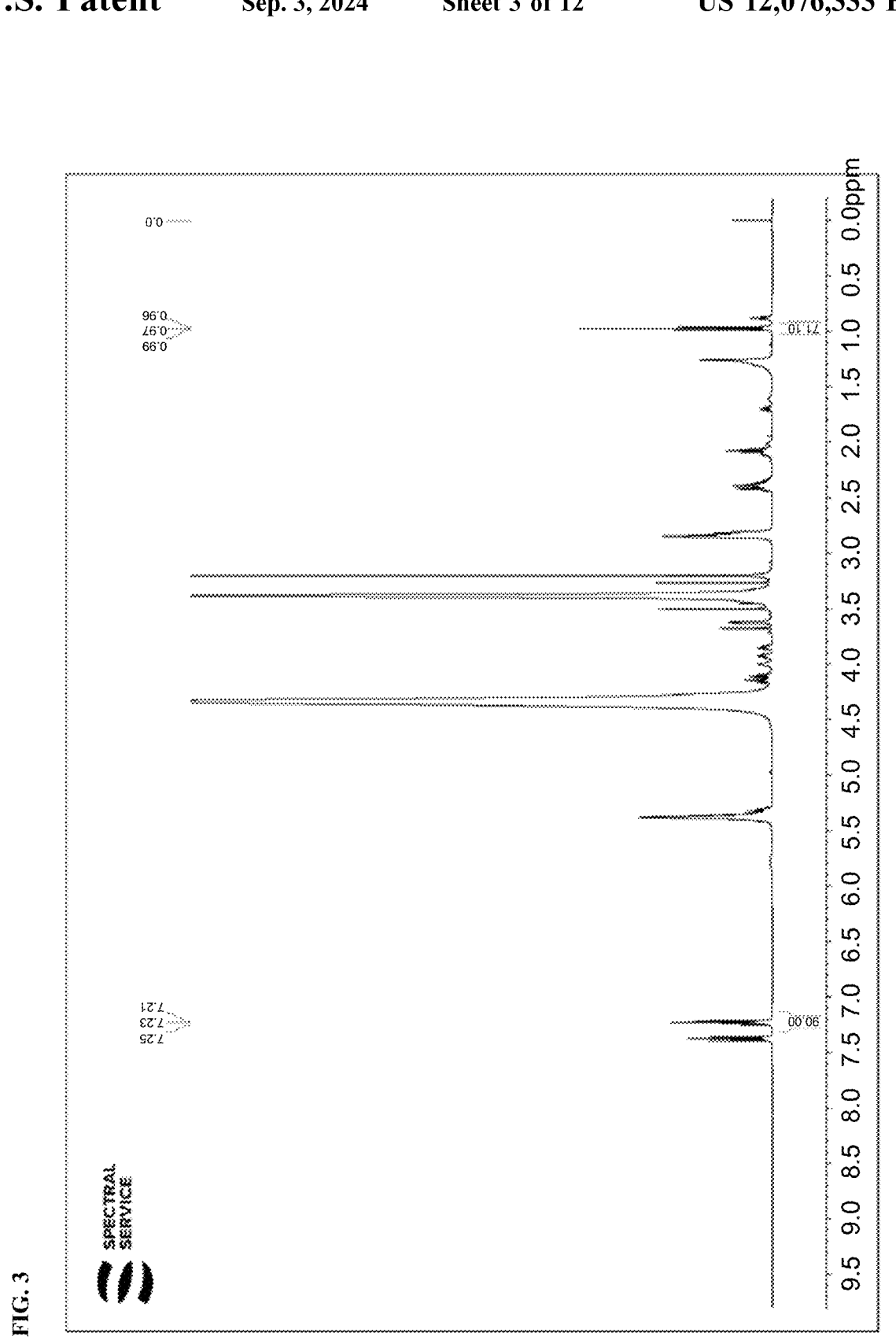
FIG. 3: $^1$H-NMR spectrum of sample AKB70005-2.
Figure 4:
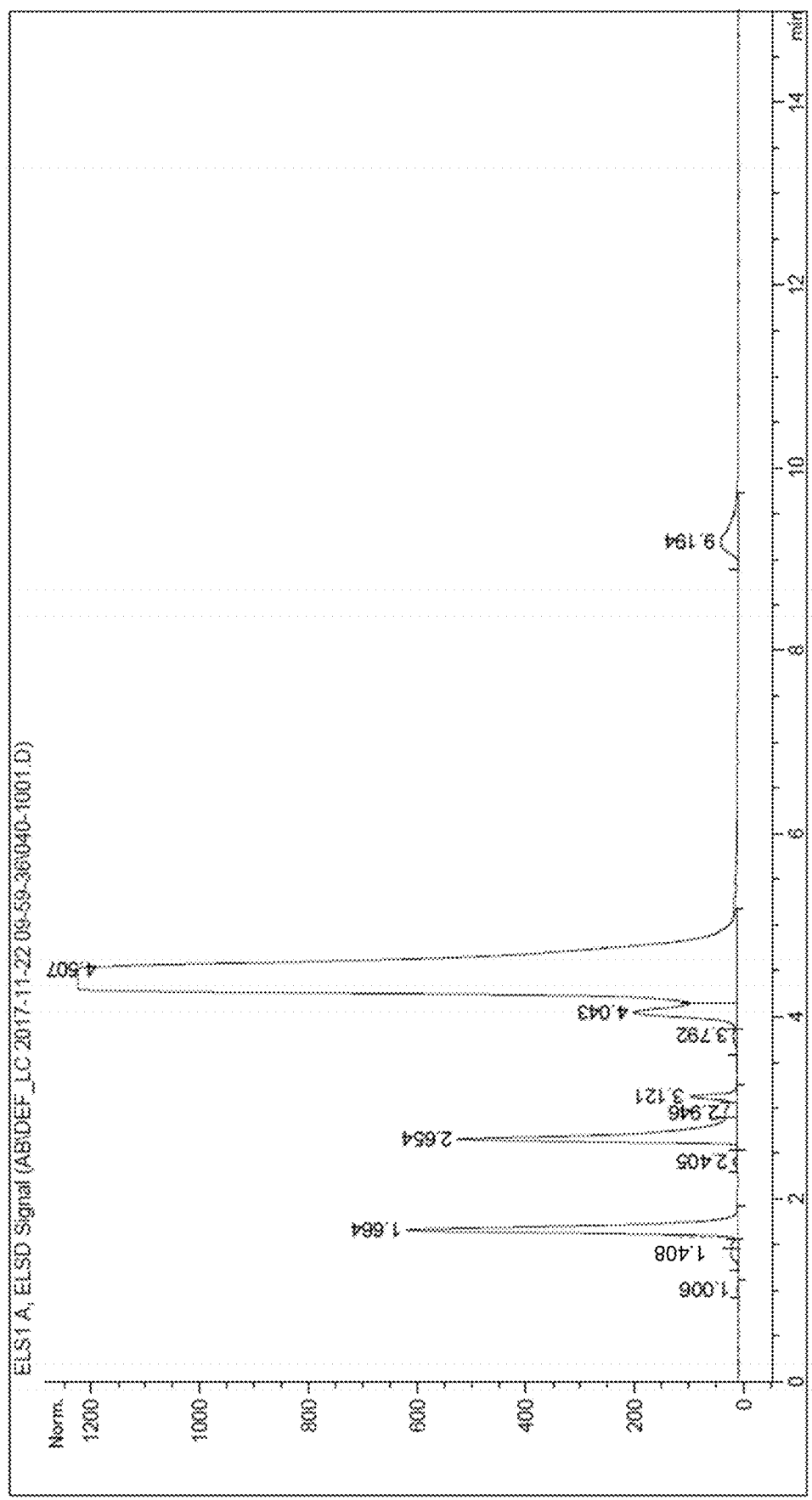
FIG. 4: HPLC chromatogram of LPC product, sample AKB70005-2.

An LPC composition produced by methods of the present invention was analyzed by $^1$H-, $^{31}$P-, 2D-NMR, TLC, GC and HPLC as appropriate. $^1$H-NMR and HPLC results are shown in FIG. 1 and FIG. 2, respectively, denoted AKB6444-1.

$^{31}$P- and 2D-NMR were used to determine the phospholipid components the results are presented in Table 1, Table 2 and Table 3 denoted AKB6444-1.

Example 2—SUPERBA™ BOOST™ Pre-WASH & FLASH

This example describes the production of a LPC composition using SUPERBA™ BOOST™ (Aker Biomarine AS, Lysaker, NO) as the starting phospholipid source. The SUPERBA™ BOOST™ is preferably produced by the SMB processes described elsewhere herein. SUPERBA™ BOOST™ is a krill phospholipid composition wherein 1000 mg contains 560 mg phospholipids, 150 mg EPA and 70 mg DHA. Briefly, 10 grams of SUPERBA™ BOOST™ is mixed into 100 ml EtOH and then 450 ml water is added in one-liter round bottom reaction flask purged with nitrogen. Next, 0.40 ml LECITASE™ Ultra is added and the reaction is allowed to proceed for 40 minutes with stirring. 500 ml EtOH is then added to deactivate the enzyme and the mixture is evaporated to dryness using a rotovap. Next, a solvent-based separation is performed. The enzyme-treated krill lipid sample is mixed with a solvent bath with heptane and methanol. The LPC and PC species migrate into the polar solvent (methanol) and the nonpolar lipids partition into the heptane. Specifically, to the dried sample was added methanol (250 ml) and heptane (250 ml). After vigorous shaking the phases were separated and the methanol phase extracted with another portion of heptane (250 ml). The heptane fractions were analyzed by TLC and evaporated separately. To the methanol residue was added silica gel 60 (20 g) and the solution concentrated to dryness. The LPC is then purified from the dried lipid composition by flash chromatography. The silica gel was loaded onto a column (diameter 5 cm) with silica gel (130 g) and the column eluted. Fraction volume 25 ml. Eluents: 500 ml EtOAc, 250 ml EtOAc:MeOH 80:20, 250 ml EtOAc:MeOH 50:50, 250 ml MeOH, 500 ml MeOH:Et3N 95:5, 500 ml MeOH:Et3N 90:10. Fractions were analyzed by TLC and evaporated according to the findings. LPC containing fractions after chromatographic separation yielded a final mass of 3.28 grams.

Figure 7:
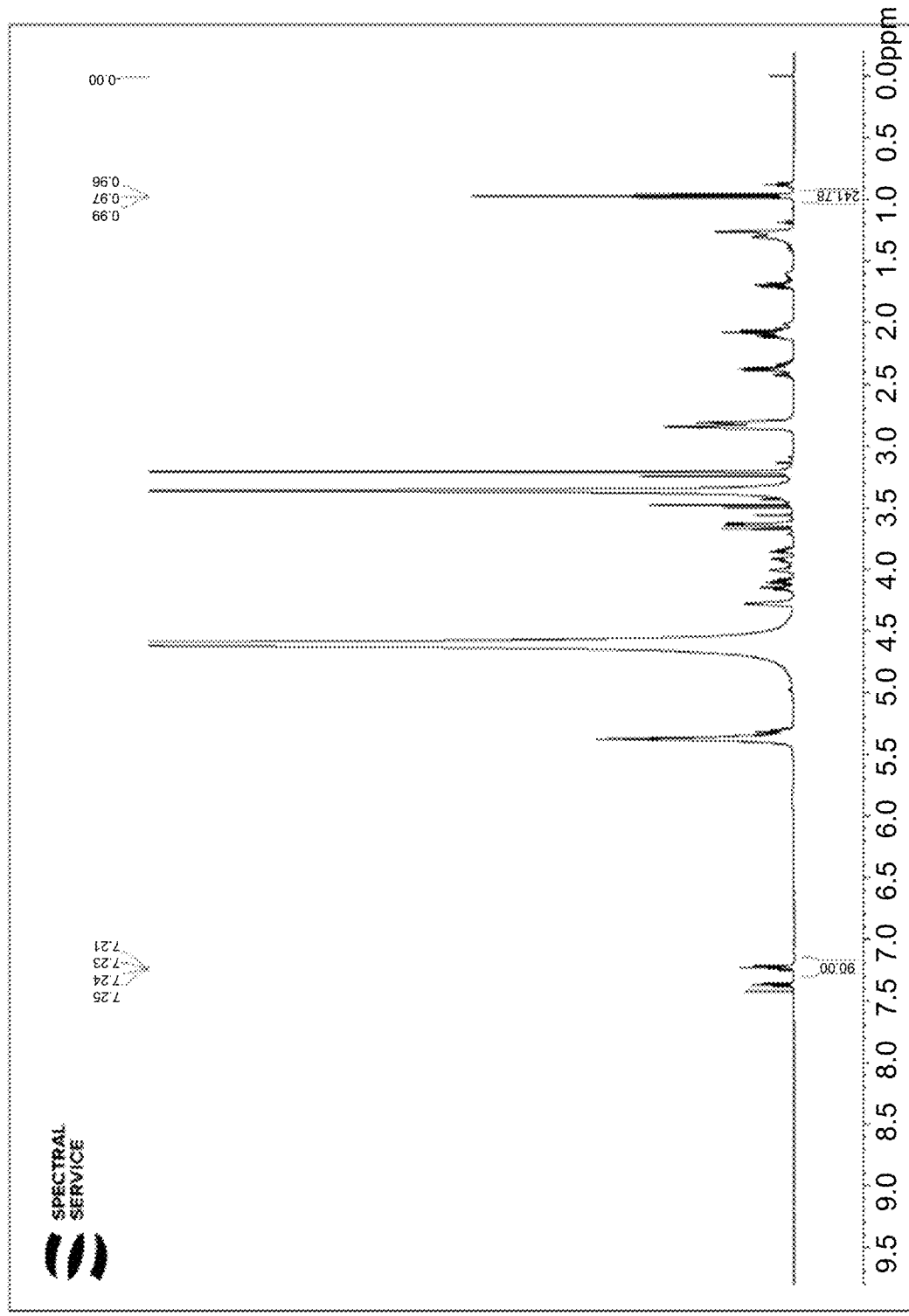
FIG. 7: $^1$H-NMR spectrum of sample AKB70005-4.
Figure 8:
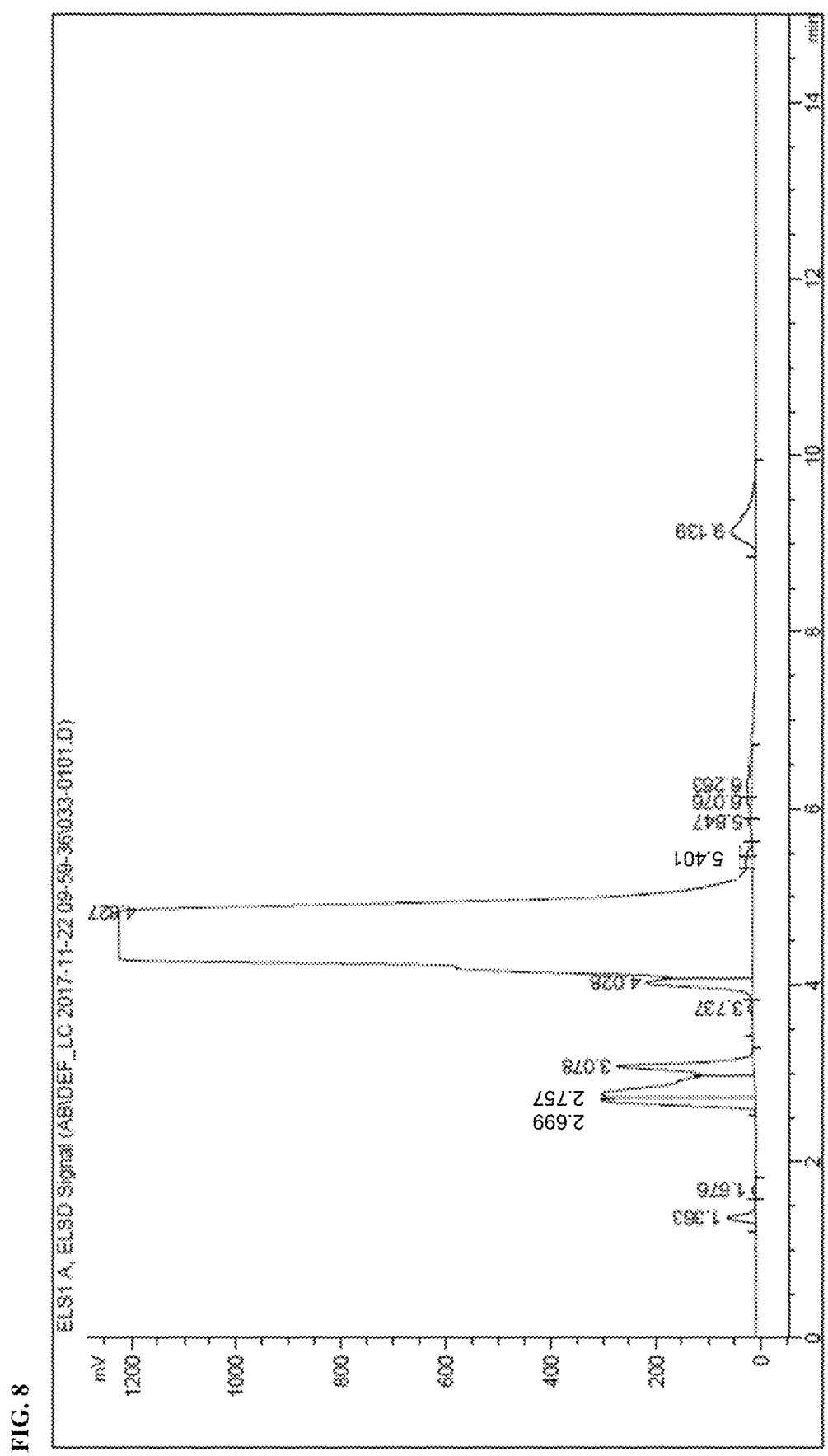
FIG. 8: HPLC chromatogram of LPC product, sample AKB70005-4.

An LPC composition produced by methods of the present invention was analyzed by $^1$H-, $^{31}$P, 2D-NMR, TLC, GC and HPLC as appropriate. $^1$H-NMR and HPLC results are shown in FIG. 7 and FIG. 8, respectively, denoted AKB70005-4.

$^{31}$P- and 2D-NMR were used to determine the phospholipid components the results are presented in Table 5, Table 9 and Table 10 denoted AKB70005-4.

Example 3—SUPERBA™ BOOST™ FLASH

This example describes the production of a LPC composition using SUPERBA™ BOOST™ (Aker Biomarine AS, Lysaker, NO) as the starting phospholipid source. The SUPERBA™ BOOST™ is preferably produced by the SMB processes described elsewhere herein. SUPERBA™ BOOST™ is a krill phospholipid composition wherein 1000 mg contains 560 mg phospholipids, 150 mg EPA and 70 mg DHA. Briefly, 10 grams of SUPERBA™ BOOST™ is mixed into 100 ml EtOH and then 450 ml water is added in one liter round bottom reaction flask purged with nitrogen. Next, 0.40 ml LECITASE™ Ultra is added and the reaction is allowed to proceed for 40 minutes with stirring. 500 ml EtOH is then added to deactivate the enzyme and the mixture is evaporated to dryness using a rotovap. Next, the LPC is then purified from the dried lipid composition by flash chromatography as follows: The residue was re-dissolved in methanol (200 ml) and silica gel 60 (20 g) added and the suspension concentrated to dryness on the rotary evaporator. The silica gel was loaded onto a column (diameter 5 cm) with silica gel (130 g) and the column eluted. Fraction volume 25 ml. Eluents: 500 ml EtOAc, 250 ml EtOAc:MeOH 80:20, 250 ml EtOAc:MeOH 50:50, 250 ml MeOH, 500 ml MeOH:Et3N 90:10. Fractions were analyzed by TLC and evaporated according to the findings. LPC containing fractions after chromatographic separation yielded a final mass of 3.73 grams.

Figure 9:
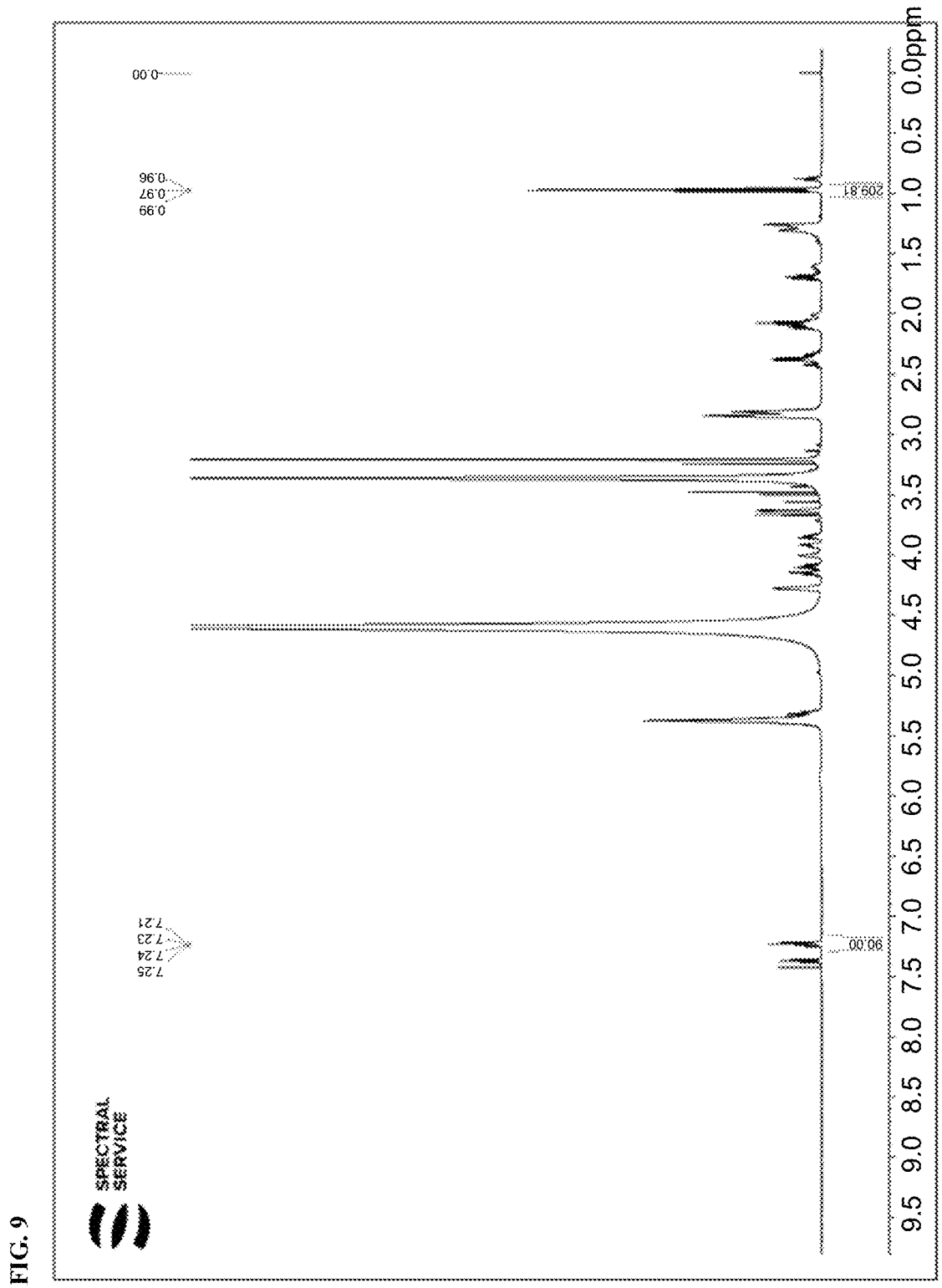
FIG. 9: $^1$H-NMR spectrum of sample AKB70005-5.
Figure 10:
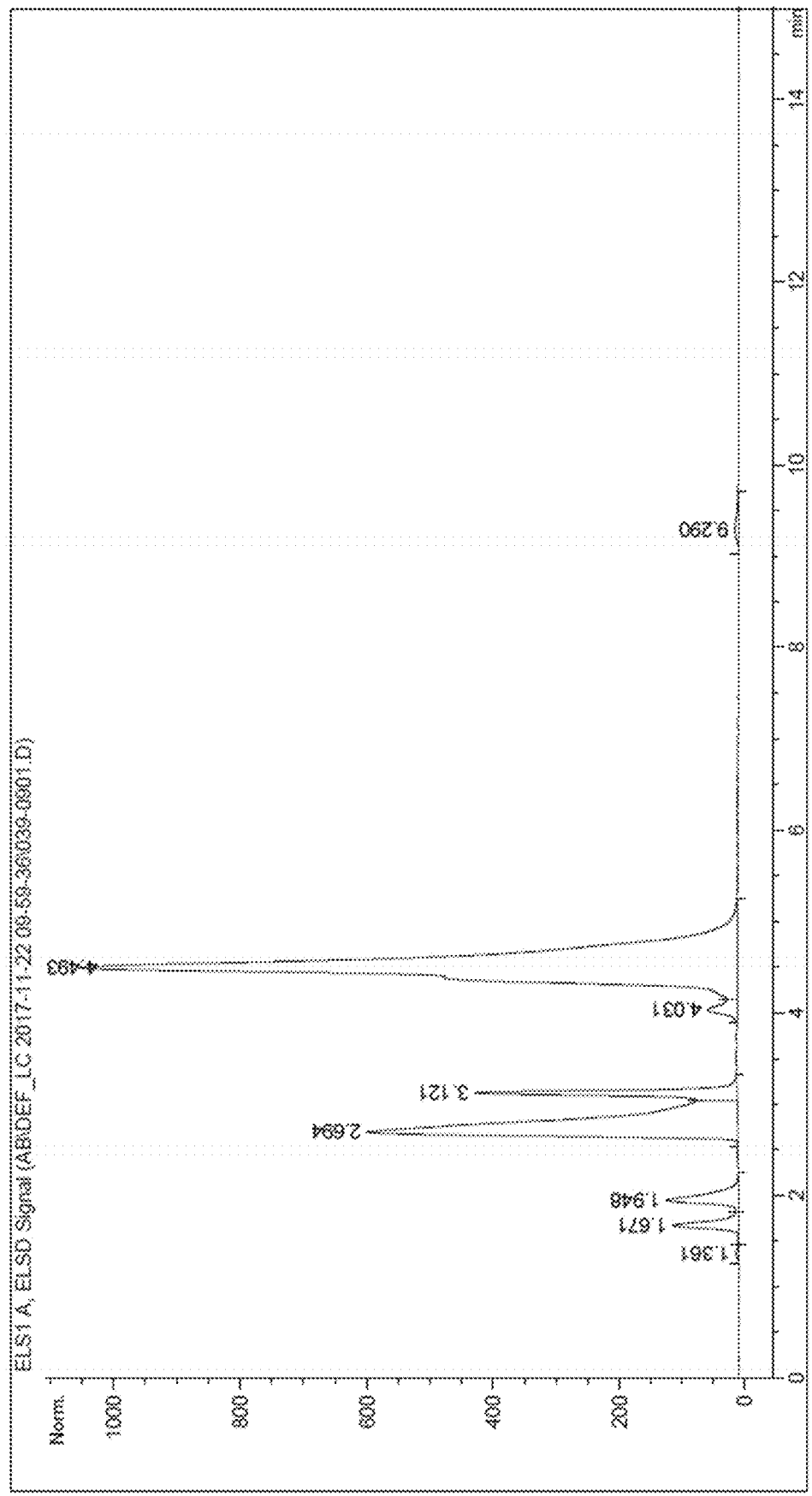
FIG. 10: HPLC chromatogram of LPC product, sample AKB70005-5.

An LPC composition produced by methods of the present invention was analyzed by $^1$H-, $^{31}$P-, 2D-NMR, TLC, GC and HPLC as appropriate. $^1$H-NMR and HPLC results are shown in FIG. 9 and FIG. 10, respectively, denoted AKB70005-5.

$^{31}$P- and 2D-NMR were used to determine the phospholipid components the results are presented in Table 6, Table 9 and Table 10 denoted AKB70005-5.

Example 4—ROMEGA™ Pre-Wash & FLASH

This example describes the production of a LPC composition using ROMEGA™ (Arctic Nutrition AS, Ørsta, NO) as the starting phospholipid source. The ROMEGA™ is preferably produced by processes described elsewhere. ROMEGA™ is a herring roe oil and fish oil composition wherein 1000 mg/3000 mg contains 340 mg/1020 mg phospholipids, 100 mg/300 mg EPA and 320 mg/960 mg DHA. Briefly, 9 grams of ROMEGA™ is mixed into 90 ml EtOH and then 450 ml water is added in one liter round bottom reaction flask purged with nitrogen. Next, 0.40 ml LECITASE™ Ultra is added and the reaction is allowed to proceed for 40 minutes with stirring. 500 ml EtOH is then added to deactivate the enzyme and the mixture is evaporated to dryness using a rotovap. Next, a solvent-based separation is performed. The enzyme-treated herring roe/fish lipid sample is mixed with a solvent bath with heptane and methanol. The LPC and PC species migrate into the polar solvent (methanol) and the nonpolar lipids partition into the heptane. Specifically, to the dried sample was added methanol (250 ml) and heptane (250 ml). After vigorous shaking the phases were separated and the methanol phase extracted with another portion of heptane (250 ml). The heptane fractions were analyzed by TLC and evaporated separately. To the methanol residue was added silica gel 60 (20 g) and the solution concentrated to dryness. The LPC is then purified from the dried lipid composition by flash chromatography. The silica gel was loaded onto a column (diameter 5 cm) with silica gel (130 g) and the column eluted. Fraction volume 25 ml. Eluents: 500 ml EtOAc, 250 ml EtOAc: MeOH 80:20, 250 ml EtOAc:MeOH 50:50, 250 ml MeOH, 500 ml MeOH:Et3N 95:5, 500 ml MeOH:Et3N 90:10. Fractions were analyzed by TLC and evaporated according to the findings. LPC containing fractions after chromatographic separation yielded a final mass of 0.84 grams.

Figure 5:
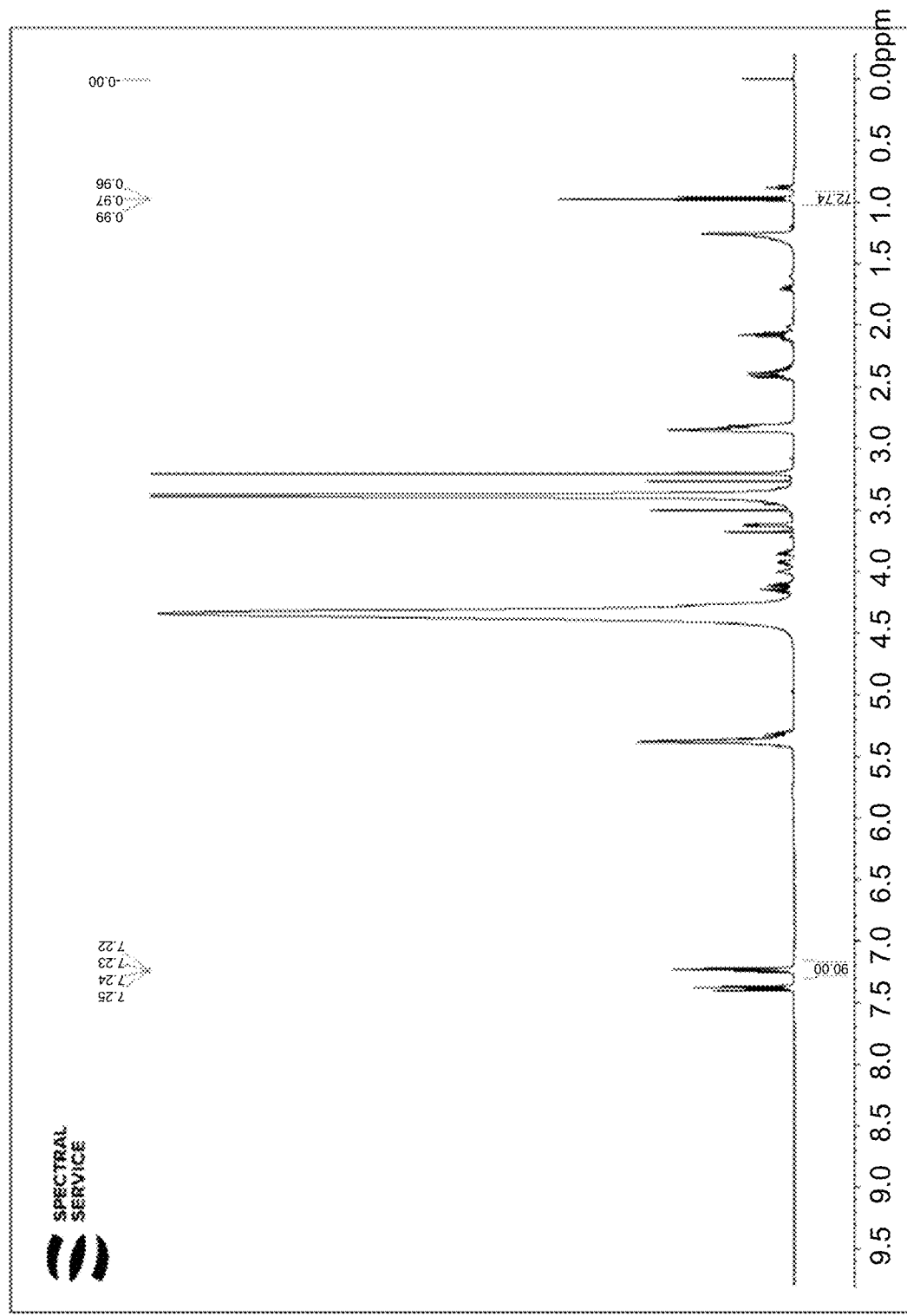
FIG. 5: $^1$H-NMR spectrum of sample AKB70005-3.
Figure 6:
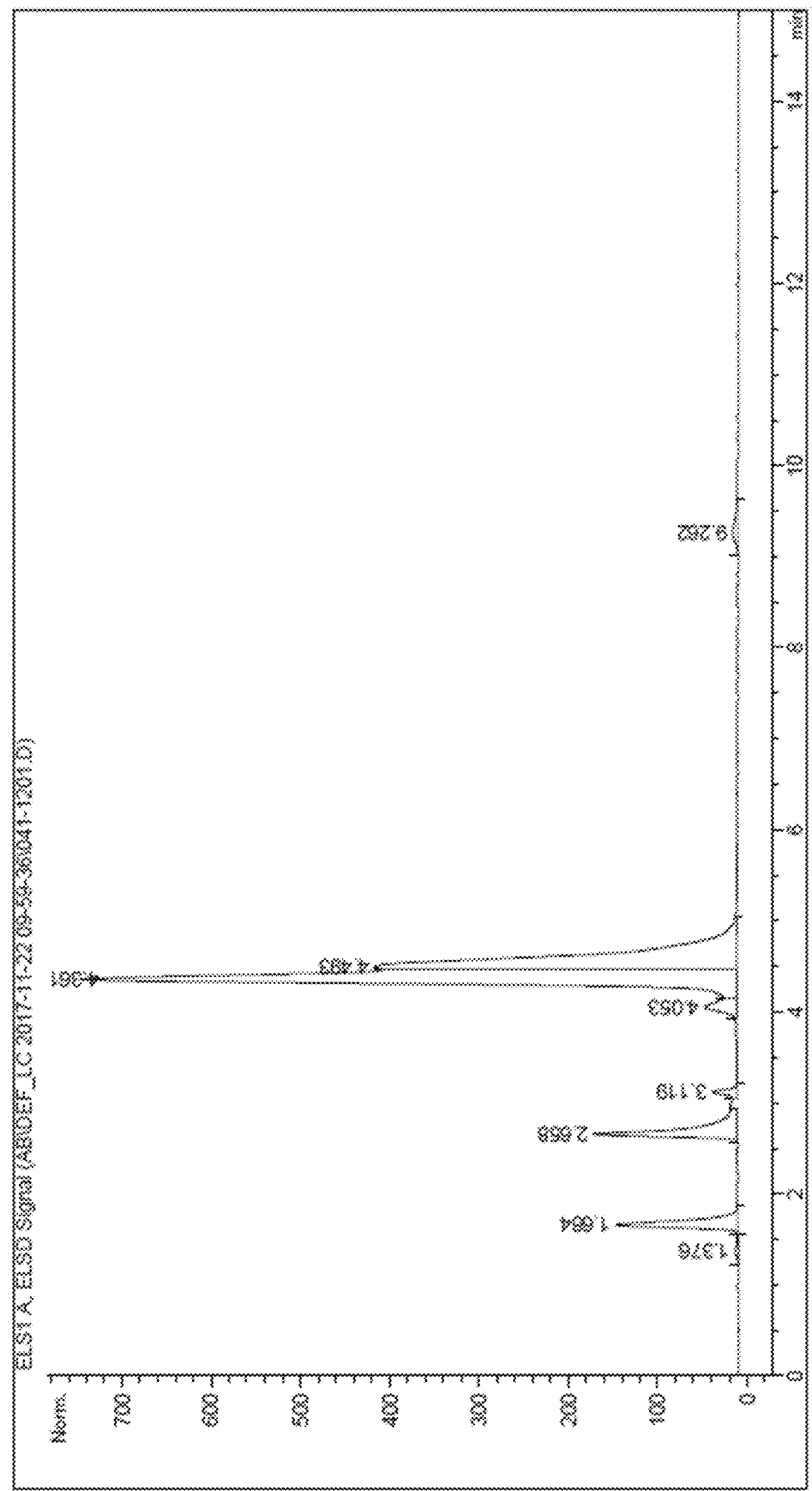
FIG. 6: HPLC chromatogram of LPC product of sample AKB70005-3.

An LPC composition produced by methods of the present invention was analyzed by $^1$H-, $^{31}$P, 2D-NMR, TLC, GC and HPLC as appropriate. $^1$H-NMR and HPLC results are shown in FIG. 5 and FIG. 6, respectively, denoted AKB70005-3.

$^{31}$P- and 2D-NMR were used to determine the phospholipid components the results are presented in Table 5, Table 7 and Table 8 denoted AKB70005-3.

Example 5—ROMEGA™ FLASH

This example describes the production of a LPC composition using ROMEGA™ (Arctic Nutrition AS, Ørsta, NO) as the starting phospholipid source. The ROMEGA™ is preferably produced by a process described elsewhere. ROMEGA™ is a herring roe oil and fish oil composition wherein 1000 mg/3000 mg contains 340 mg/1020 mg phospholipids, 100 mg/300 mg EPA and 320 mg/960 mg DHA. Briefly, 9 grams of ROMEGA™ is mixed into 90 ml EtOH and then 450 ml water is added in one-liter round bottom reaction flask purged with nitrogen. Next, 0.40 ml LECITASE™ Ultra is added and the reaction is allowed to proceed for 40 minutes with stirring. 500 ml EtOH is then added to deactivate the enzyme and the mixture is evaporated to dryness using a rotovap. Next, the LPC is then purified from the dried lipid composition by flash chromatography as follows: The residue was re-dissolved in methanol (200 ml) and silica gel 60 (20 g) added and the suspension concentrated to dryness on the rotary evaporator. The silica gel was loaded onto a column (diameter 5 cm) with silica gel (130 g) and the column eluted. Fraction volume 25 ml. Eluents: 500 ml EtOAc, 250 ml EtOAc:MeOH 80:20, 250 ml EtOAc:MeOH 50:50, 250 ml MeOH, 500 ml MeOH:Et3N 90:10. Fractions were analyzed by TLC and evaporated according to the findings. LPC containing fractions after chromatographic separation yielded a final mass of 0.76 grams.

An LPC composition produced by methods of the present invention was analyzed by 1H-, 31P-, 2D-NMR, TLC, GC and HPLC as appropriate. $^1$H-NMR and HPLC results are shown in FIG. 5 and FIG. 6, respectively, denoted AKB70005-2.

$^{31}$P- and 2D-NMR were used to determine the phospholipid components the results are presented in Table 4, Table 7 and Table 8 denoted AKB70005-2.

TABLE 1

Results (summary), 2D- and 31P-NMR (PLs) of sample AKB69444-1

| Component | Method | Weight Percent | |
|---|---|---|---|
| PC | $^{31}$P-NMR | 3.04 | — |
| 1-LPC | $^{31}$P-NMR | 5.73 | — |
| 2-LPC | $^{31}$P-NMR | 75.38 | — |
| PI | $^{31}$P-NMR | 0.00 | — |
| PS-Na | $^{31}$P-NMR | 0.00 | — |
| PE | $^{31}$P-NMR | 0.00 | — |
| LPE | $^{31}$P-NMR | 0.00 | — |
| APE | $^{31}$P-NMR | 0.00 | — |
| PG | $^{31}$P-NMR | 0.00 | — |
| DPG | $^{31}$P-NMR | 0.00 | — |
| PA | $^{31}$P-NMR | 0.00 | — |
| LPA | $^{31}$P-NMR | 0.00 | — |
| other PL | $^{31}$P-NMR | 0.34 | — |
| sum | $^{31}$P-NMR | 84.15 | — |
| phosphorus | $^{31}$P-NMR | 4.83 | — |

TABLE 2

Results (summary), 2D- and 31P-NMR (ether PLs) of sample AKB69444-1

| Component | Method | Weight Percent | |
|---|---|---|---|
| PC | $^{31}$P-NMR | 1.90 | — |
| PC-ether | $^{31}$P-NMR | 1.10 | — |
| 2-LPC | $^{31}$P-NMR | 57.20 | — |
| 2-LPC-ether | $^{31}$P-NMR | 18.20 | — |
| other PL | $^{31}$P-NMR | 0.34 | — |
| sum | $^{31}$P-NMR | 84.15 | — |
| phosphorus | $^{31}$P-NMR | 4.83 | — |

TABLE 3

The LPC composition contained 38.74% omega-3 fatty acids w/w of the composition as determined by $^1$H-NMR of sample AKB69444-1.

| Test Item | Integral TI | Initial weight [mg] TI | Integral IS | Initial weight [mg] IS | mMoi IS | MMoi TI | Content [mg] TI | Content [%] TI |
|---|---|---|---|---|---|---|---|---|
| AKB67919-1 | 198.61 | 350.65 | 90.00 | 20.43 | 0.0626 | 0.4141 | 135.8263 | 38.74 |
| Int. Standard | Molecular weight TI | 328.00 | | | | | | |
| TPP | Molecular weight IS | 326.29 | | | | | | |
| Rounding | Number of atoms TI | 3 | | | | | | |
| 4 | Number of atoms IS | 9 | | | | | Balance | XPE-841 |
| en | Content [%] IS | 99.9 | | | | | Mettlet-Toledo | XPE205DR/M |
| | Comment: Initial weight is higher than required MinWeigh of 10 mg. | | | | | | | |

*) calculated as DHA. contains mixture of any w-3 FA (omega 3 fatty acids)

TABLE 4

Omega-3 fatty acids w/w of the LPC composition as determined by $^1$H-NMR for the samples AKB70005-1 and AKB70005-2.

| components | test method | AKB70005-1 specification Romega AB:ABM-1:1 weight-% | AKB70005-2 specification Lecitase Romega AB:ABM-1:3 Flash weight-% |
|---|---|---|---|
| omega 3 FA *) | $^1$H-NMR | 43.56 | — | 43.78 | — |

*) calculated as DHA, contains mixture of any w-3 FA (omega 3 fatty acids)

TABLE 5

Omega-3 fatty acids w/w of the LPC composition as determined by $^1$H-NMR for the samples AKB70005-3 and AKB70005-4.

| components | test method | AKB70005-3 specification Lecitase Romega MS:ABM-1:47 pre/flash weight-% | | AKB70005-4 specification Lecitase Boost MS:ABM-1:43B pre/flash weight-% | |
|---|---|---|---|---|---|
| omega 3 FA *) | $^1$H-NMR | 42.85 | — | 47.55 | — |

*) calculated as DHA, contains mixture of any w-3 FA (omega 3 fatty acids)

TABLE 6

Omega-3 fatty acids w/w of the LPC composition as determined by $^1$H-NMR for the sample AKB70005-5.

| components | test method | AKB70005-5 specification Lecitase Boost MS:ABM-1:45B flash weight-% | |
|---|---|---|---|
| omega 3 FA *) | $^1$H-NMR | 47.06 | — |

*) calculated as DHA, contains mixture of any w-3 FA (omega 3 fatty acids)

TABLE 7

Results (summary), 2D- and 31P-NMR (PLs) for AKB70005-1, AKB70005-2 and AKB70005-3.

| components | test method | AKB70005-1 specification Romega AB:ABM-1:1 weight % | | AKB70005-2 specification Lecitase Romega AB:ABM-1:3 Flash weight % | | AKB70005-3 specification Lecitase Romega MS:ABM-1:47 pre/flash weight % | |
|---|---|---|---|---|---|---|---|
| PC | $^{31}$P-NMR | 20.97 | — | 5.03 | — | 7.29 | — |
| 1-LPC | $^{31}$P-NMR | 0.25 | — | 6.66 | — | 6.41 | — |
| 2-LPC | $^{31}$P-NMR | 2.06 | — | 59.95 | — | 56.42 | — |
| PI | $^{31}$P-NMR | 0.35 | — | 0.00 | — | 0.00 | — |
| SPH | $^{31}$P-NMR | 0.69 | — | 3.70 | — | 4.34 | — |
| PE | $^{31}$P-NMR | 1.73 | — | 0.00 | — | 0.00 | — |
| LPE | $^{31}$P-NMR | 0.25 | — | 0.00 | — | 0.00 | — |
| APE | $^{31}$P-NMR | 0.00 | — | 0.00 | — | 0.00 | — |
| PG | $^{31}$P-NMR | 0.00 | — | 0.00 | — | 0.00 | — |
| DPG | $^{31}$P-NMR | 0.00 | — | 0.00 | — | 0.00 | — |
| PA | $^{31}$P-NMR | 0.09 | — | 0.00 | — | 0.26 | — |
| LPA | $^{31}$P-NMR | 0.00 | — | 0.00 | — | 0.00 | — |
| other PL | $^{31}$P-NMR | 0.00 | — | 0.55 | — | 0.00 | — |
| sum | $^{31}$P-NMR | 26.39 | — | 75.88 | — | 74.73 | — |
| phosphorus | $^{31}$P-NMR | 1.06 | — | 4.21 | — | 4.10 | — |

TABLE 8

Results (summary), 2D- and 31P-NMR (PLs) for AKB70005-1, AKB70005-2 and AKB70005-3.

| components | test method | AKB70005-1 specification Romega AB:ABM-1:1 weight % | | AKB70005-2 specification Lecitase Romega AB:ABM-1:3 Flash weight % | | AKB70005-3 specification Lecitase Romega MS:ABM-1:47 pre/flash weight % | |
|---|---|---|---|---|---|---|---|
| PC | $^{31}$P-NMR | 20.20 | — | 2.40 | — | 3.50 | — |
| PC-ether | $^{31}$P-NMR | 0.80 | — | 2.70 | — | 3.80 | — |
| 2-LPC | $^{31}$P-NMR | 1.40 | — | 58.50 | — | 55.10 | — |
| 2-LPC-ether | $^{31}$P-NMR | 0.60 | — | 1.00 | — | 0.80 | — |
| 2-LPC-plasma | $^{31}$P-NMR | 0.00 | — | 0.50 | — | 0.50 | — |
| PE | $^{31}$P-NMR | 1.60 | — | 0.00 | — | 0.00 | — |
| PE-ether | $^{31}$P-NMR | 0.20 | — | 0.00 | — | 0.00 | — |

TABLE 9

Results (summary), 2D- and 31P-NMR (PLs) for AKB70005-4 and AKB70005-5.

| components | test method | AKB70005-4 specification Lecitase Boost MS:ABM-1:43B pre/flash weight-% | | AKB70005-5 specification Lecitase Boost MS:ABM-1:45B flash weight-% | |
|---|---|---|---|---|---|
| PC | $^{31}$P-NMR | 9.24 | — | 3.44 | — |
| 1-LPC | $^{31}$P-NMR | 7.24 | — | 7.37 | — |
| 2-LPC | $^{31}$P-NMR | 63.04 | — | 68.64 | — |
| PI | $^{31}$P-NMR | 0.00 | — | 0.00 | — |
| PS-Na | $^{31}$P-NMR | 0.00 | — | 0.00 | — |
| PE | $^{31}$P-NMR | 0.00 | — | 0.00 | — |
| LPE | $^{31}$P-NMR | 0.00 | — | 0.00 | — |
| APE | $^{31}$P-NMR | 0.00 | — | 0.00 | — |
| PG | $^{31}$P-NMR | 0.00 | — | 0.00 | — |
| DPG | $^{31}$P-NMR | 0.00 | — | 0.00 | — |
| PA | $^{31}$P-NMR | 0.00 | — | 0.00 | — |
| LPA | $^{31}$P-NMR | 0.00 | — | 0.00 | — |
| other PL | $^{31}$P-NMR | 0.00 | — | 0.00 | — |
| sum | $^{31}$P-NMR | 79.52 | — | 79.45 | — |
| phosphorus | $^{31}$P-NMR | 4.43 | — | 4.54 | — |

TABLE 10

Results (summary), 2D- and 31P-NMR (PLs) for AKB70005-4 and AKB70005-5.

| components | test method | AKB70005-4 specification Lecitase Boost MS:ABM-1:43B pre/flash weight-% | | AKB70005-5 specification Lecitase Boost MS:ABM-1:45B flash weight-% | |
|---|---|---|---|---|---|
| PC | $^{31}$P-NMR | 4.70 | — | 1.90 | — |
| PC-ether | $^{31}$P-NMR | 4.60 | — | 1.60 | — |
| 2-LPC | $^{31}$P-NMR | 60.30 | — | 65.50 | — |
| 2-LPC-ether | $^{31}$P-NMR | 1.70 | — | 1.60 | — |
| 2-LPC-plasma | $^{31}$P-NMR | 1.00 | — | 1.60 | — |
| PE | $^{31}$P-NMR | 0.00 | — | 0.00 | — |
| PE-ether | $^{31}$P-NMR | 0.00 | — | 0.00 | — |

TABLE 11

Legend (abbreviations).

| abbreviation | full name |
|---|---|
| 1-LPC | 1-lyso-phosphatidylcholine |
| 2-LPC | 2-lyso-phosphatidylcholine |
| APE | N-acyl-phosphatidylethanolamine |
| CDCl$_3$ | chloroform-d$_1$ |
| Cs$_2$CO$_3$ | caesium carbonate |
| DHA | docosahexaenoic acid |
| D$_2$O | deuteriumoxide |
| DPG | diphosphatidylglycerol |
| EDTA | ethylenediaminetetraacetic |
| FA | fatty acid |
| IS | internal standard |
| LPA | lyso-phosphatidic acid |
| LPI | lyso-Phosphatidylinositol |
| LPS | lyso-Phosphatidylserine |
| MeOD | methanol-d$_4$ |
| NMR | nuclear magnetic resonance |
| PA | phosphatidic acid |
| PC | phosphatidylcholine |
| PE | phosphatidylethanolamine |
| PG | phosphatidylglycerol |
| PI | phosphatidylinositol |
| PL | phospholipid |
| PS | phosphatidylserine |
| SPH | sphingomyelin |
| TMS | tetramethylsilane |
| TPP | triphenyl phosphate |
| w-3 FA | omega 3 fatty acid |

Example 6

An LPC composition was produced using SUPERBA™ krill oil as a starting point. The phospholipid content was analyzed by $^{31}$P-NMR. The results are presented in Table 12.

TABLE 12

| Phospholipid | Weight-% | Mol-% | MW [g/mol] |
|---|---|---|---|
| PC | 7.73 | 15.08 | 790.0 |
| 1-LPC | 10.23 | 29.50 | 534.5 |
| 2-LPC | 17.51 | 50.47 | 534.5 |
| PI | —*) | —*) | 907.0 |
| LPI | —*) | —*) | 629.5 |
| PS-Na | —*) | —*) | 833.0 |
| LPS | —*) | —*) | 555.5 |
| SPH | —*) | —*) | 812.0 |
| PE | 0.48 | 0.96 | 770.0 |
| LPE | 0.96 | 3.00 | 492.5 |
| APE | —*) | —*) | 1032.0 |
| PG | —*) | —*) | 820.0 |
| DPG | —*) | —*) | 774.0 |
| PA | —*) | —*) | 746.0 |
| LPA | —*) | —*) | 468.5 |
| Other PL | 0.52 | 0.99 | 812.0 |
| Sum | 37.44 | 100.00 | |
| Phosphorus | 2.01 | | |

Comment: Integrals of Phospholipid signals, which are not evaluable or belong to not listed Phospholipids, are recorded as "other". *)-not observed, no signal assignment

Example 7

This example provides a summary of production of further lysophospholipid compositions of the invention.

Method of Synthesizing LPC Species from Krill Oil

The methods used to synthesize LPC from krill oil may be divided in four steps depending on target composition of final mixture/sample:

1. CRUDE: a process that allows a concentration of 14-27.3 weight % LPC in the final composition to be achieved (Table 13.1-1 and 14.1-1).
2. POLAR-1/POLAR-2: a process after CRUDE that allows a concentration of 35.2-65.7 weight % LPC in the final composition to be achieved (Table 13.1-2 and 14.1-2).
3. FLASH: a process after CRUDE that allows a concentration of 56.6-81.1 weight % LPC in the final composition to be achieved (Table 13.1-3).
4. FORMULATION: a process after POLAR-2 that allows a concentration of 39.3-41.1 weight % LPC with 5-14 weight % PEG400 in the final composition to be achieved (14.1-3).

Figure 11:
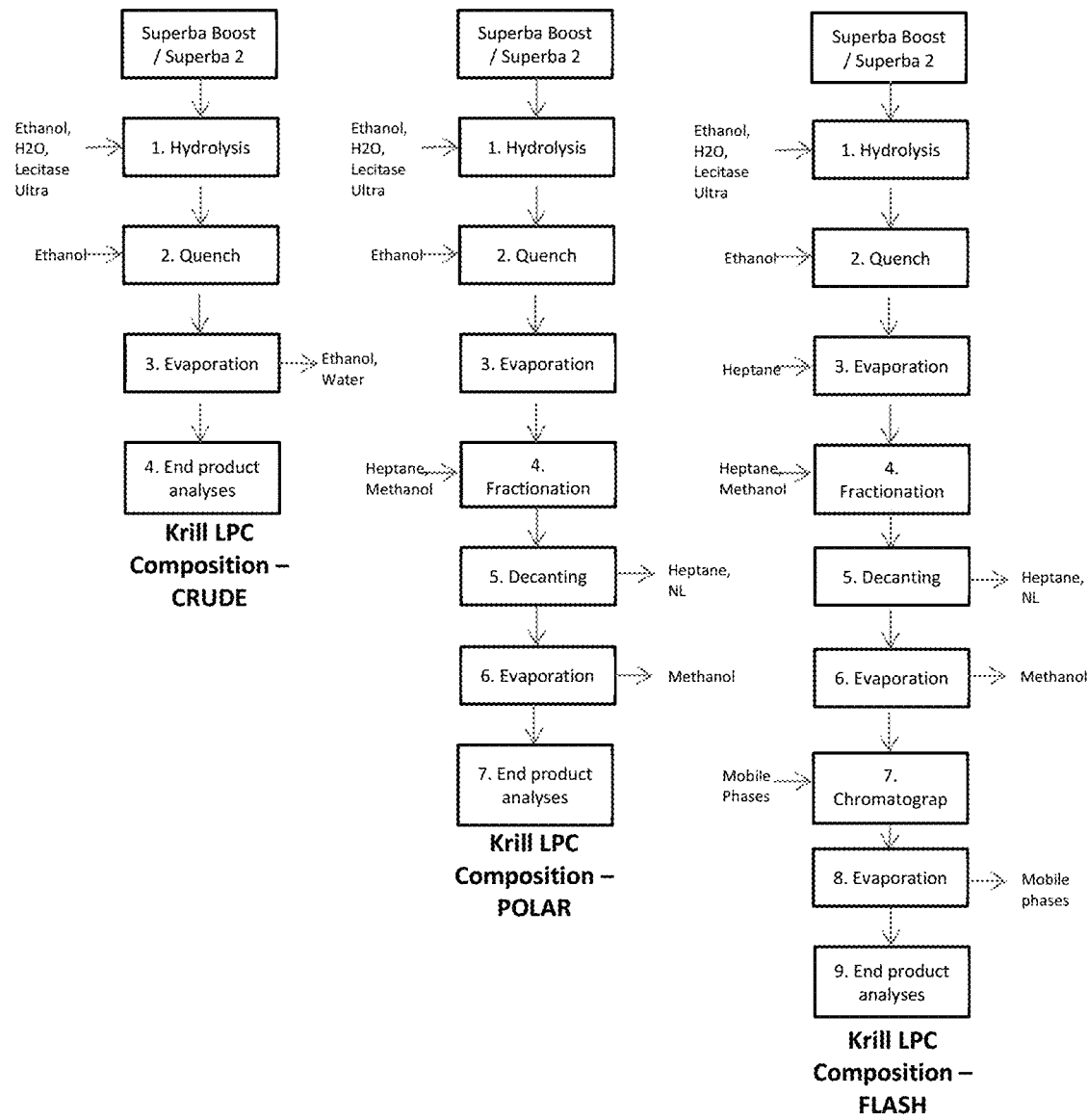
FIG. 11: Flow chart of processes of the present invention.
Figure 12:
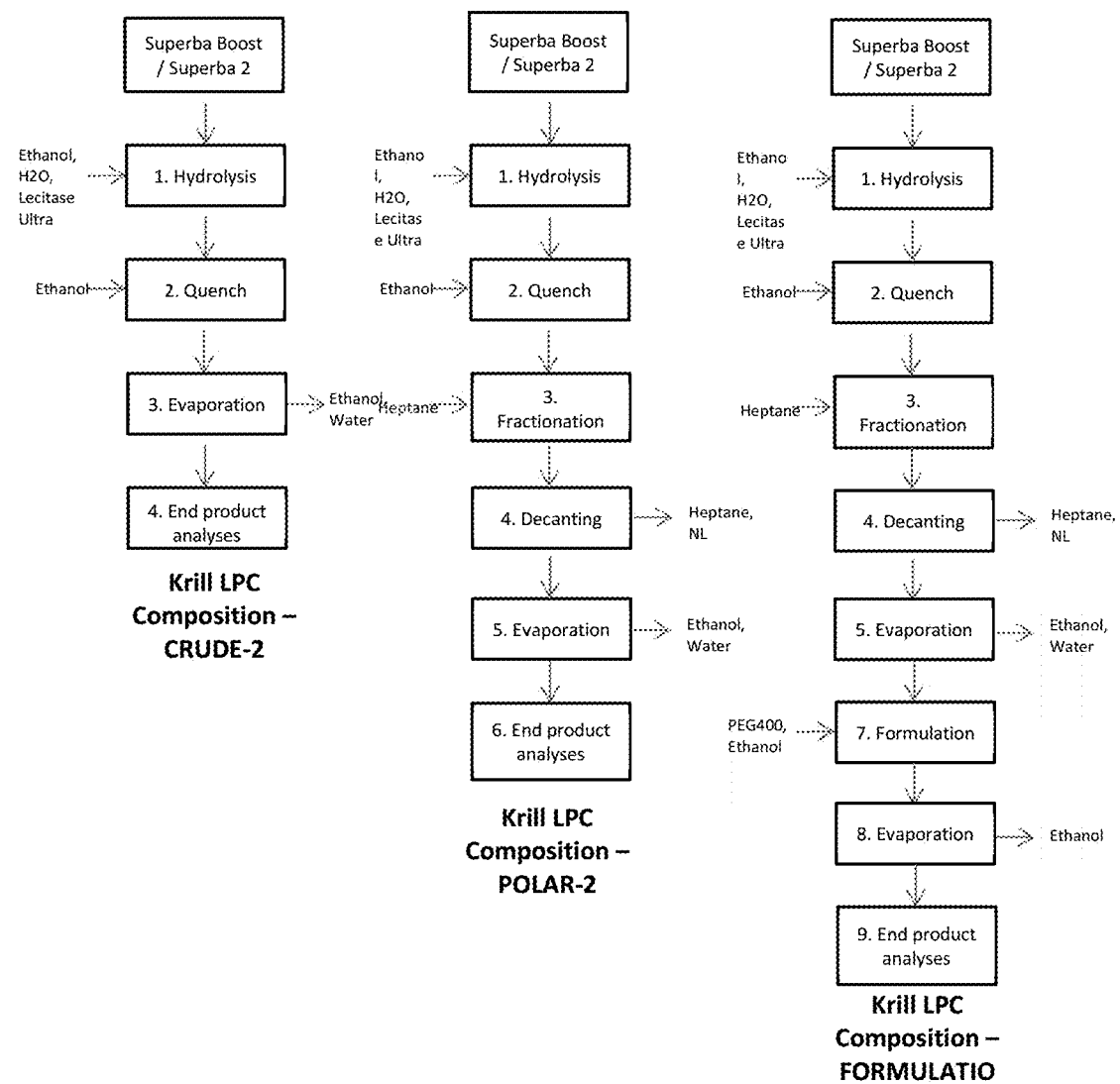
FIG. 12: Flow chart of processes of the present invention.

FLASH and POLAR are alternative processes to achieve an LPC enrichment of CRUDE-1 and CRUDE-2 LPC mixtures/samples, whereas FORMULATION is a process that allows for a formulation with POLAR-2 LPC mixtures/samples with PEG. Flow diagrams of the various processes are provided as FIGS. 11 (Process 1) and 12 (Process 2).

1. Crude Samples:

CRUDE-1 & CRUDE-2 LPC Mixtures/Samples Follow the Same Processes.

Superba Boost (10 g) was dissolved in EtOH (2-10 g), diluted with pH stabilized water (2-45 g, pH 6-12) to achieve a mixture pH of 5.2-6.2, added Lecitase ultra 40 μl, capped and stirred at room temperature for 120-1440 minutes. To prevent oxidation, samples may be flushed with N2. The reaction mixture was quenched with addition of EtOH (25-50 g) and concentrated under reduced pressure at 50° C. to afford the CRUDE-1 and CRUDE-2 LPC-mixtures/samples (Tables 13 and 16, respectively).

2. Polar-1/Polar-2 Samples:

POLAR-2: The POLAR process was initiated directly after quench in the CRUDE process. Thus, the CRUDE sample was not concentrated under reduced pressure at 50° C. to afford the CRUDE-1 and CRUDE-2 LPC-mixtures/batches, rather, 25-100 g of heptane was added to the CRUDE-1 or CRUDE-2 mixture to achieve a phase separation and thus an enrichment of polar lipids in the EtOH and water rich phase, called the polar phase. The heptane phase was decanted leaving only the polar phase. The polar phase was concentrated under reduced pressure to afford the POLAR-1 and POLAR-2 LPC-mixtures/samples (Tables 14 and 17, respectively).

3. FLASH Samples:

The CRUDE samples were re-dissolved in ethanol (10-100 g) with addition of 25-50 g Silica gel 60 and evaporated to dryness. Flash chromatography (125 g Silicagel 60, column diameter 5 cm) was performed. Elution with 500 ml 80:20 MPA:MPB, 500 ml 50:50 MPA:MPB, 500 ml MP B, 500 ml MP C was performed. The column was subsequently extruded with EtOH:Et3N (80:20, 300 mL). Based on the results different fractions were combined and evaporated to afford the FLASH LPC-mixtures/samples (Table 15).

4. FORMULATION Samples:

A formulation with PEG400 was made of the POLAR mixtures/samples. For this, EtOH and PEG400 was added to the POLAR mixture whereby the mixture (EtOH, PEG400 and POLAR LPC mixture) was concentrated under reduced pressure at 50° C. to afford the FORMULATION LPC-mixtures/samples (Table 18) with a final concentration of 5-14 weight % PEG400 and 4-7 weight % EtOH (Table 18).

TABLE 13

Analytical results from six CRUDE-1 krill LPC composition batches from Process 1

| Parameter | CRUDE-1 Batch number | | | | | |
|---|---|---|---|---|---|---|
| | AKB:ABM-1:7B | AKB:ABM-1:9B | AKB:ABM-1:13 | AKB:ABM-1:15 | MS:ABM-1:65 | MS:ABM-1:69 |
| Phospholipid comp, weight %, $^{31}$P NMR | | | | | | |
| PC | 4.9 | 5.7 | 7.8 | 5.1 | 4.3 | 10.8 |
| PC-ether | 2.8 | 4.2 | 4.3 | 4.2 | 3.5 | 4.8 |
| 1-LPC | 5.0 | 8.6 | 6.6 | 6.3 | 10.2 | 10.7 |
| 2-LPC | 9.1 | 16.6 | 17.3 | 20.7 | 17.2 | 16.2 |
| 2-LPC-ether | <0.1 | <0.1 | <0.1 | <0.1 | 0.3 | 0.4 |
| PE | 0.2 | 0.4 | 0.2 | 0.2 | <0.1 | 0.4 |
| PE-ether | <0.1 | <0.1 | <0.1 | 0.5 | 0.5 | 0.4 |
| LPE | 0.3 | 0.7 | 0.3 | <0.1 | 1.0 | 0.9 |
| Other | 0.7 | 0.9 | 1.0 | 1.1 | 0.5 | 0.4 |
| Sum total PL | 23.0 | 37.1 | 37.4 | 38.1 | 37.5 | 45.0 |
| Sum total LPC | 14.1 | 25.2 | 23.9 | 27.0 | 27.7 | 27.3 |
| Phosphorus | 1.2 | 1.9 | 1.9 | 2.0 | 2.1 | 2.3 |
| Fatty acids, g/100 g, GC | | | | | | |
| 12:0 | Not | | | | <0.1 | <0.1 |
| 14:0 | Available | | | | 3.7 | 3.9 |
| 15:0 | | | | | 0.2 | 0.2 |
| 16:0 | | | | | 12.5 | 13.3 |
| 16:1n7 | | | | | 2.2 | 2.3 |
| 18:0 | | | | | 0.7 | 0.7 |
| 18:1n9 | | | | | 4.3 | 4.5 |
| 18:1n7 | | | | | 3.6 | 3.8 |
| 18:2n6 | | | | | 0.9 | 0.9 |
| 18:3n3 | | | | | 1.4 | 1.5 |

TABLE 13-continued

Analytical results from six CRUDE-1 krill LPC composition batches from Process 1

| | CRUDE-1 Batch number | | | | | |
|---|---|---|---|---|---|---|
| Parameter | AKB:ABM-1:7B | AKB:ABM-1:9B | AKB:ABM-1:13 | AKB:ABM-1:15 | MS:ABM-1:65 | MS:ABM-1:69 |
| 18:4n3 | | | | | 2.6 | 2.7 |
| 20:1n9 | | | | | 0.3 | 0.3 |
| 20:4n6 | | | | | 0.2 | 0.2 |
| 20:3n3 | | | | | <0.1 | <0.1 |
| 20:4n3 | | | | | 0.3 | 0.4 |
| 20:5n3 | | | | | 15.2 | 16.0 |
| 22:1n9 | | | | | 0.5 | 0.5 |
| 21:5n3 | | | | | 0.5 | 0.5 |
| 22:5n3 | | | | | 0.3 | 0.3 |
| 22:6n3 | | | | | 7.6 | 7.9 |
| Unknown | | | | | 3.2 | 3.4 |
| Saturated fatty acids | | | | | 17.1 | 18.1 |
| Monoenic fatty acids | | | | | 10.9 | 11.4 |
| PUFA (n-6) fatty acids | | | | | 1.1 | 1.1 |
| PUFA (n-3) fatty acids | | | | | 27.9 | 29.2 |
| Total-PUFA fatty acids | | | | | 29.0 | 30.3 |
| Fatty acids total | | | | | 60.2 | 63.2 |

TABLE 14

Analytical results from six POLAR-1 krill LPC composition batches from Process 1

| | POLAR-1 Batch number | | | | | |
|---|---|---|---|---|---|---|
| Parameter | AKB:ABM-1:7B | AKB:ABM-1:9B | AKB:ABM-1:13 | AKB:ABM-1:15 | MS:ABM-1:65 | MS:ABM-1:69 |
| Phospholipid comp, weight %, $^{31}$P NMR | | | | | | |
| PC | 11.7 | 7.8 | 11.1 | 7.1 | 8.5 | Not available |
| PC-ether | 5.0 | 5.7 | 6.0 | 6.0 | 9.4 | |
| 1-LPC | 8.9 | 12.4 | 7.0 | 9.0 | 28.8 | |
| 2-LPC | 26.3 | 28.5 | 33.7 | 33.8 | 35.9 | |
| 2-LPC-ether | <0.1 | <0.1 | <0.1 | <0.1 | 1.0 | |
| PE | <0.1 | 0.4 | 0.4 | 0.2 | <0.1 | |
| PE-ether | <0.1 | <0.1 | <0.1 | <0.1 | 0.9 | |
| LPE | <0.1 | 1.1 | 1.1 | 0.8 | 1.8 | |
| Other | 2.1 | 1.9 | 2.2 | 2.2 | <0.1 | |
| Sum total PL | 54.0 | 57.8 | 61.4 | 59.1 | 86.3 | |
| Sum total LPC | 35.2 | 40.9 | 40.7 | 42.8 | 65.7 | |
| Phosphorus | 1.2 | 1.9 | 1.9 | 2.0 | 4.7 | |
| Fatty acids, g/100 g, GC | | | | | Not available | |
| 12:0 | <0.1 | <0.1 | <0.1 | <0.1 | | |
| 14:0 | 1.1 | 2.0 | 1.4 | 1.4 | | |
| 15:0 | 0.1 | 0.1 | 0.1 | 0.1 | | |
| 16:0 | 6.2 | 8.5 | 8.4 | 7.9 | | |
| 16:1n7 | 0.9 | 1.4 | 1.1 | 1.1 | | |
| 18:0 | 0.6 | 0.6 | 0.7 | 0.7 | | |
| 18:1n9 | 2.4 | 3.2 | 2.7 | 2.7 | | |
| 18:1n7 | 1.6 | 2.3 | 2.3 | 2.1 | | |
| 18:2n6 | 0.6 | 0.8 | 0.7 | 0.7 | | |
| 18:3n3 | 1.1 | 1.5 | 1.4 | 1.3 | | |
| 18:4n3 | 1.3 | 2.2 | 2.0 | 2.0 | | |
| 20:1n9 | 0.1 | 0.2 | 0.2 | 0.1 | | |
| 20:4n6 | 0.2 | 0.3 | 0.3 | 0.2 | | |
| 20:3n3 | <0.1 | <0.1 | <0.1 | <0.1 | | |
| 20:4n3 | 0.2 | 0.4 | 0.4 | 0.3 | | |
| 20:5n3 | 11.4 | 18.8 | 18.2 | 17.4 | | |
| 22:1n9 | 0.2 | 0.3 | 0.3 | 0.3 | | |
| 21:5n3 | 0.4 | 0.6 | 0.6 | 0.6 | | |
| 22:5n3 | 0.2 | 0.4 | 0.4 | 0.3 | | |

TABLE 14-continued

Analytical results from six POLAR-1 krill LPC composition batches from Process 1

| Parameter | POLAR-1 Batch number | | | | | |
|---|---|---|---|---|---|---|
| | AKB:ABM-1:7B | AKB:ABM-1:9B | AKB:ABM-1:13 | AKB:ABM-1:15 | MS:ABM-1:65 | MS:ABM-1:69 |
| 22:6n3 | 5.0 | 9.1 | 8.8 | 8.4 | | |
| Unknown | 0.7 | 1.2 | 1.0 | 1.0 | | |
| Saturated fatty acids | 7.9 | 11.2 | 10.6 | 10.1 | | |
| Monoenic fatty acids | 5.2 | 7.3 | 6.5 | 6.4 | | |
| PUFA (n-6) fatty acids | 0.8 | 1.1 | 1.0 | 1.0 | | |
| PUFA (n-3) fatty acids | 19.6 | 33.0 | 31.7 | 30.3 | | |
| Total-PUFA fatty acids | 20.4 | 34.1 | 32.6 | 31.3 | | |
| Fatty acids total | 34.3 | 53.9 | 50.8 | 48.7 | | |

TABLE 15

Analytical results from six FLASH krill LPC composition batches from Process 1

| Parameter | FLASH Batch number | | | | | | |
|---|---|---|---|---|---|---|---|
| | MS-ABM1-31 | MS:ABM-1:43B | MS:ABM-1:45B | MS:ABM-1:65 | MS:ABM-1:67 | MS:ABM-1:69 | MS:ABM-1:71 |
| Phospholipid comp, weight %, $^{31}$P NMR | | | | | | | |
| PC | 1.9 | 4.7 | 1.9 | 3.3 | 1.8 | 13.7 | 6.7 |
| PC-ether | 1.1 | 4.6 | 1.6 | 3.8 | 1.6 | 5.6 | 3.1 |
| 1-LPC | 5.7 | 7.2 | 7.4 | 8.7 | 8.0 | 7.0 | 7.1 |
| 2-LPC | 57.2 | 60.3 | 65.5 | 68.5 | 55.0 | 48.6 | 58.3 |
| 2-LPC-ether | 18.2 | 2.7 | 3.2 | 1.4 | 1.2 | 1.0 | 1.6 |
| PE | <0.1 | <0.1 | <0.1 | <0.1 | <0.1 | <0.1 | <0.1 |
| PE-ether | <0.1 | <0.1 | <0.1 | <0.1 | <0.1 | <0.1 | <0.1 |
| LPE | <0.1 | <0.1 | <0.1 | <0.1 | <0.1 | <0.1 | <0.1 |
| Other | 0.3 | <0.1 | <0.1 | <0.1 | 0.5 | 0.6 | <0.1 |
| Sum total PL | 84.2 | 79.5 | 79.5 | 85.7 | 68.1 | 76.5 | 76.8 |
| Sum total LPC | 81.1 | 70.2 | 76.1 | 78.6 | 64.2 | 56.6 | 67.0 |
| Phosphorus | 4.8 | 4.4 | 4.5 | 4.9 | 3.9 | 4.1 | 4.3 |
| Fatty acids, g/100 g, GC | Not available | | Not available | | | | |
| 12:0 | | <0.1 | | <0.1 | 0.2 | <0.1 | <0.1 |
| 14:0 | | 0.2 | | 0.2 | 0.2 | 0.4 | 0.3 |
| 15:0 | | <0.1 | | <0.1 | <0.1 | <0.1 | <0.1 |
| 16:0 | | 1.0 | | 1.4 | 1.4 | 4.4 | 3.4 |
| 16:1n7 | | 0.6 | | 0.6 | 0.6 | 0.7 | 0.6 |
| 18:0 | | 0.2 | | 0.4 | 0.5 | 0.5 | 0.5 |
| 18:1n9 | | 2.5 | | 2.4 | 2.6 | 2.7 | 2.6 |
| 18:1n7 | | 0.4 | | 0.5 | 0.5 | 1.2 | 0.9 |
| 18:2n6 | | 0.9 | | 0.9 | 1.0 | 0.9 | 1.0 |
| 18:3n3 | | 1.8 | | 1.9 | 2.0 | 1.8 | 1.9 |
| 18:4n3 | | 2.6 | | 2.5 | 2.6 | 2.3 | 2.3 |
| 20:1n9 | | <0.1 | | <0.1 | <0.1 | 0.1 | <0.1 |
| 20:4n6 | | 0.3 | | 0.3 | 0.3 | 0.3 | 0.3 |
| 20:3n3 | | <0.1 | | <0.1 | <0.1 | <0.1 | <0.1 |
| 20:4n3 | | 0.4 | | 0.4 | 0.4 | 0.4 | 0.4 |
| 20:5n3 | | 24.5 | | 24.3 | 24.3 | 22.0 | 21.7 |
| 22:1n9 | | <0.1 | | <0.1 | <0.1 | 0.2 | 0.2 |
| 21:5n3 | | 0.9 | | 0.9 | 0.9 | 0.8 | 0.8 |
| 22:5n3 | | 0.5 | | 0.5 | 0.5 | 0.5 | 0.5 |
| 22:6n3 | | 12.4 | | 10.5 | 10.3 | 9.8 | 9.6 |
| Unknown | | 0.4 | | 0.4 | 0.6 | 0.4 | 0.3 |
| Saturated fatty acids | | 1.4 | | 1.9 | 1.9 | 5.3 | 4.2 |
| Monoenic fatty acids | | 3.5 | | 3.5 | 3.7 | 4.8 | 4.4 |
| PUFA (n-6) fatty acids | | 1.2 | | 1.2 | 1.3 | 1.2 | 1.2 |

TABLE 15-continued

Analytical results from six FLASH krill LPC composition batches from Process 1

| | FLASH Batch number | | | | | | |
|---|---|---|---|---|---|---|---|
| Parameter | MS-ABM1-31 | MS:ABM-1:43B | MS:ABM-1:45B | MS:ABM-1:65 | MS:ABM-1:67 | MS:ABM-1:69 | MS:ABM-1:71 |
| PUFA (n-3) fatty acids | 43.1 | | 40.9 | 40.9 | 37.5 | 37.1 | |
| Total-PUFA fatty acids | 44.3 | | 42.1 | 42.1 | 38.6 | 38.3 | |
| Fatty acids total | 49.6 | | 47.9 | 48.3 | 49.1 | 47.1 | |

TABLE 16

Analytical results from two CRUDE-2 krill LPC composition batches from Process 2

| | CRUDE-2 Batch number | |
|---|---|---|
| Parameter | LS:ABM_9C0 | LS:ABM_10C0 |
| Phospholipid comp, weight %, $^{31}$P NMR | | |
| PC | 4.3 | 6.1 |
| PC-ether | 4.3 | 3.6 |
| 1-LPC | 10.7 | 4.0 |
| 2-LPC | 15.3 | 21.0 |
| 2-LPC-ether | — | — |
| PE | 0.7 | 0.9 |
| PE-ether | — | — |
| LPE | 0.9 | 1.8 |
| Other | 0.9 | 2.2 |
| Sum total PL | 37.1 | 39.5 |
| Sum total LPC | 26.0 | 25.0 |
| Phosphorus | 2.0 | 2.1 |
| Total PL gravimetric | 42.0 | 45.3 |
| Total NL gravimetric | 58.0 | 54.7 |
| H$_2$O %, w/w | 1.0 | 0.5 |
| Fatty acids, g/100 g, GC | | |
| 12:0 | 0.2 | 0.1 |
| 14:0 | 4.4 | 4.6 |
| 15:0 | 0.2 | 0.2 |
| 16:0 | 13.5 | 14.3 |
| 16:1n7 | 2.1 | 4.1 |
| 18:0 | 1.3 | 1.7 |
| 18:1n9 | 4.8 | 5.3 |
| 18:1n7 | 4.0 | 3.8 |
| 18:2n6 | 1.0 | 0.8 |
| 18:3n3 | 1.7 | 0.5 |
| 18:4n3 | 3.7 | 1.5 |
| 20:1n9 | 0.3 | 0.4 |
| 20:4n6 | 0.2 | 0.2 |
| 20:3n3 | 0.1 | 0.1 |
| 20:4n3 | 0.5 | 0.3 |
| 20:5n3 | 16.0 | 17.8 |
| 22:1n9 | 0.4 | 0.8 |
| 21:5n3 | 0.5 | 0.6 |
| 22:5n3 | 0.4 | 0.3 |
| 22:6n3 | 8.6 | 6.8 |
| Unknown | 0 | 0 |
| Saturated fatty acids | 19.5 | 20.9 |
| Monoenic fatty acids | 11.5 | 14.4 |
| PUFA (n-6) fatty acids | 1.2 | 1.0 |
| PUFA (n-3) fatty acids | 31.4 | 27.9 |
| Total-PUFA fatty acids | 32.6 | 28.8 |
| Fatty acids total | 63.7 | 64.1 |

TABLE 17

Analytical results from eight POLAR-2 krill LPC composition batches from Process 2

| | POLAR-2 Batch number | | | | | | | |
|---|---|---|---|---|---|---|---|---|
| Parameter | LS:ABM_3 K | LS:ABM_3 D | LS:ABM_8 A1 | LS:ABM_8 B1 | LS:ABM_8 C1 | LS:ABM_8 D1-1 | LS:ABM_9 A1 | LS:ABM_9 C1 |
| Phospholipid comp, weight %, $^{31}$P NMR | | | | | | | | |
| PC | 8.4 | 5.8 | 7.5 | 10.8 | 6.3 | 12.2 | 9.4 | 8.4 |
| PC-ether | 5.5 | 3.4 | 7.5 | 7.9 | 5.4 | 5.8 | 7.9 | 8.3 |
| 1-LPC | 15.6 | 9.4 | 25.0 | 18.0 | 12.8 | 11.2 | 18.6 | 14.1 |
| 2-LPC | 33.4 | 33.0 | 21.2 | 23.7 | 36.6 | 30.6 | 29.5 | 35.6 |
| 2-LPC-ether | <0.1 | <0.1 | <0.1 | <0.1 | <0.1 | <0.1 | <0.1 | — |
| PE | 1.2 | 0.9 | 1.2 | 1.5 | 1.1 | 1.7 | 1.2 | 1.1 |
| PE-ether | <0.1 | <0.1 | <0.1 | <0.1 | <0.1 | <0.1 | <0.1 | — |
| LPE | 2.8 | 2.4 | 1.6 | 2.9 | 2.8 | 3.0 | 1.8 | 1.7 |
| Other | 4.6 | 3.4 | 1.6 | 2.0 | 4.9 | 4.5 | 1.8 | 2.3 |
| Sum total PL | 71.5 | 58.1 | 65.7 | 66.7 | 70.0 | 68.9 | 70.1 | 71.4 |
| Sum total LPC | 49 | 42.4 | 46.2 | 41.7 | 49.4 | 41.8 | 48.1 | 49.7 |
| Phosphorus | 3.8 | 3.12 | 3.5 | 3.5 | 3.7 | 3.6 | 3.7 | 3.8 |

TABLE 17-continued

Analytical results from eight POLAR-2 krill LPC composition batches from Process 2

| Parameter | LS:ABM_3 K | LS:ABM_3 D | LS:ABM_8 A1 | LS:ABM_8 B1 | LS:ABM_8 C1 | LS:ABM_8 D1-1 | LS:ABM_9 A1 | LS:ABM_9 C1 |
|---|---|---|---|---|---|---|---|---|
| Total PL gravimetric | 77.2 | 63.4 | 76.2 | 73.7 | 76.8 | 79.4 | 77.0 | 79.0 |
| Total NL gravimetric | 22.8 | 36.6 | 23.8 | 26.3 | 23.2 | 20.6 | 23.0 | 21.0 |
| $H_2O$ %, w/w | Not available | Pending | 2.4 | 1.4 | 1.2 | 3.7 | 0.9 | 0.6 |
| Fatty acids, g/100 g, GC | | | | | | | | |
| 12:0 | | | <0.1 | <0.1 | <0.1 | <0.1 | 0.1 | 0.1 |
| 14:0 | | | 1.4 | 1.9 | 1.3 | 1.4 | 1.3 | 1.1 |
| 15:0 | | | 0.1 | 0.1 | <0.1 | <0.1 | 0.1 | 0.1 |
| 16:0 | | | 5.8 | 7.9 | 6.2 | 7.3 | 6.1 | 5.2 |
| 16:1n7 | | | 0.9 | 3.1 | 2.3 | 1.8 | 0.9 | 0.8 |
| 18:0 | | | 0.8 | 1.0 | 0.9 | 1.1 | 1.0 | 0.9 |
| 18:1n9 | | | 2.7 | 3.3 | 2.8 | 3.0 | 2.6 | 2.3 |
| 18:1n7 | | | 1.7 | 1.8 | 1.4 | 1.9 | 1.7 | 1.4 |
| 18:2n6 | | | 0.8 | 1.1 | 0.9 | 0.7 | 0.8 | 0.7 |
| 18:3n3 | | | 1.5 | 0.4 | 0.5 | 0.5 | 1.5 | 1.4 |
| 18:4n3 | | | 2.6 | 1.2 | 2.0 | 1.4 | 2.7 | 2.5 |
| 20:1n9 | | | 0.3 | 0.3 | 0.3 | 0.3 | 0.1 | 0.1 |
| 20:4n6 | | | 0.2 | 0.4 | 0.3 | 0.2 | 0.2 | 0.2 |
| 20:3n3 | | | 0.1 | <0.1 | <0.1 | <0.1 | 0.1 | 0.1 |
| 20:4n3 | | | 0.4 | 0.4 | 0.4 | 0.3 | 0.4 | 0.4 |
| 20:5n3 | | | 18.8 | 20.4 | 21.4 | 21.5 | 18.7 | 16.8 |
| 22:1n9 | | | 0.2 | 0.3 | 0.4 | 0.4 | 0.2 | 0.2 |
| 21:5n3 | | | 0.7 | 0.7 | 0.8 | 0.9 | 0.6 | 0.6 |
| 22:5n3 | | | 0.4 | 0.5 | 0.4 | 0.4 | 0.4 | 0.4 |
| 22:6n3 | | | 10.3 | 9.2 | 9.9 | 8.7 | 10.1 | 8.9 |
| Unknown | | | 1.6 | 2.1 | 1.7 | 1.7 | <0.1 | <0.1 |
| Saturated fatty acids | | | 8.1 | 10.8 | 8.4 | 9.8 | 8.6 | 7.3 |
| Monoenic fatty acids | | | 5.9 | 8.8 | 7.1 | 7.3 | 5.4 | 4.8 |
| PUFA (n-6) fatty acids | | | 1.0 | 1.5 | 1.2 | 0.9 | 1.0 | 0.9 |
| PUFA (n-3) fatty acids | | | 34.8 | 32.7 | 35.3 | 33.6 | 34.5 | 30.9 |
| Total-PUFA fatty acids | | | 35.8 | 34.1 | 36.5 | 34.6 | 35.5 | 31.8 |
| Fatty acids total | | | 51.4 | 55.8 | 53.6 | 53.3 | 49.6 | 44.0 |

TABLE 18

Analytical results from two Formulation krill LPC composition batches from Process 2

| Parameter | LS:ABM_9A2 | LS:ABM_9C2 |
|---|---|---|
| Phospholipid comp, weight %, $^{31}$P NMR | | |
| PC | 7.7 | 6.9 |
| PC-ether | 6.4 | 6.6 |
| 1-LPC | 15.0 | 12.6 |
| 2-LPC | 24.3 | 28.5 |
| 2-LPC-ether | — | — |
| PE | 1.1 | 1.1 |
| PE-ether | — | — |
| LPE | 1.3 | 1.4 |
| Other | 1.1 | 1.4 |
| Sum total PL | 57.0 | 58.5 |
| Sum total LPC | 39.3 | 41.1 |
| Phosphorus | 3.0 | 3.1 |
| Fatty acids, g/100 g, GC | | |
| 12:0 | 0.1 | 0.1 |
| 14:0 | 1.2 | 1.0 |
| 15:0 | 0.1 | 0.1 |
| 16:0 | 5.3 | 4.8 |
| 16:1n7 | 0.7 | 0.7 |
| 18:0 | 1.0 | 1.0 |
| 18:1n9 | 2.2 | 2.1 |
| 18:1n7 | 1.4 | 1.3 |
| 18:2n6 | 0.7 | 0.7 |
| 18:3n3 | 1.3 | 1.3 |
| 18:4n3 | 2.3 | 2.4 |
| 20:1n9 | 0.1 | 0.1 |
| 20:4n6 | 0.2 | 0.2 |
| 20:3n3 | 0.1 | 0.1 |
| 20:4n3 | 0.3 | 0.4 |
| 20:5n3 | 15.8 | 16.6 |
| 22:1n9 | 0.2 | 0.2 |
| 21:5n3 | 0.5 | 0.6 |
| 22:5n3 | 0.3 | 0.3 |
| 22:6n3 | 8.4 | 9.1 |
| Unknown | <0.1 | <0.1 |
| Saturated fatty acids | 7.5 | 6.9 |
| Monoenic fatty acids | 4.6 | 4.4 |
| PUFA (n-6) fatty acids | 0.8 | 0.9 |
| PUFA (n-3) fatty acids | 29.2 | 30.7 |
| Total-PUFA fatty acids | 30.1 | 31.6 |
| Fatty acids total | 42.2 | 42.9 |

Table 19 provides additional analytical data for the various batches.

TABLE 19

|  | CRUDE-2 batches | | POLAR-2 batches | | FORMULATION batches | |
| --- | --- | --- | --- | --- | --- | --- |
|  | LS:ABM_ 9C0 | LS:ABM_ 10C0 | LS:ABM_ 9A1 | LS:ABM_ 9C1 | LS:ABM_ 9A2 | LS:ABM_ 9C2 |
| Salt (NaCl) (ppm) | 490.4 | 3262.4 | 1051.7 | 941.6 | 999.5 | 839.6 |
| Astaxanthin (µg/g) | 123.2 | 190.8 | 75.5 | 82.8 | 90.1 | 74.2 |
| Conductivity (µS/cm) | 15.6 | 64.4 | 20.3 | 16.3 | 62.0 | 52.8 |

Example 9

This example provides data on the uptake of a lysophospholipid compositions of the present invention in biological tissues. Briefly, the LS:ABM-9C0 lysophospholipid composition described above was spiked with $^{14}$C-labelled lysoPC-EPA or lysoPC-DHA and compared to a purified krill PC composition (98% PC formulated with PEG) spiked with $^{14}$C-labelled PC-EPA or DHA. The spiked compositions were orally administered to rats and the uptake into various tissues was measured by Quantitative Whole Body Autoradiography. Data was collected both on the timing of uptake in various organs and tissues as well as the amount of incorporation into the tissue. The results are provided in Tables 20-23. Surprisingly, these data indicate that uptake of both the lysoPC-EPA spiked lysophospholipid composition and lysoPC-DHA spiked lysophospholipid composition was both faster in time and greater in total amount of EPA and DHA incorporated as compared to the samples that were prepared with intact phospholipids (i.e., samples that did not contain any appreciable amount of lysophospholipids). This result was observed in all investigated organs/tissues except the eye.

TABLE 20

| EPA-PC | | Time after administration (hrs) | | | | | | | |
| --- | --- | --- | --- | --- | --- | --- | --- | --- | --- |
| | | 0.5 | 3 | 8 | 24 | 72 | 96 | 168 | 336 |
| (% of dose/organ) | Adrenal gland | <0.001 | 0.009 | 0.016 | 0.008 | 0.011 | 0.008 | 0.007 | 0.003 |
| | Blood | 0.082 | 0.971 | 1.012 | 0.267 | 0.302 | 0.269 | 0.191 | 0.122 |
| | Bone | <0.014 | 0.236 | 0.414 | 0.162 | 0.259 | 0.234 | 0.257 | 0.16 |
| | Bone marrow | 0.001 | 0.05 | 0.099 | 0.059 | 0.108 | 0.058 | 0.044 | 0.017 |
| | Brain | <0.001 | 0.01 | 0.025 | 0.028 | 0.088 | 0.102 | 0.118 | 0.147 |
| | Eye (whole) | <0.001 | 0.002 | 0.003 | 0.001 | 0.006 | 0.006 | 0.004 | 0.005 |
| | Fat (white) | <0.015 | 0.956 | 6.599 | 1.936 | 2.515 | 2.811 | 2.651 | 0.995 |
| | Kidney (whole) | 0.006 | 0.127 | 0.216 | 0.119 | 0.195 | 0.194 | 0.122 | 0.069 |
| | Large intestine mucosa | <0.002 | 0.886 | 0.23 | 0.162 | 0.16 | 0.162 | 0.108 | 0.059 |
| | Liver | 0.103 | 5.526 | 10.551 | 3.188 | 2.472 | 2.082 | 1.286 | 0.0639 |
| | Lung | 0.005 | 0.115 | 0.181 | 0.074 | 0.106 | 0.089 | 0.074 | 0.038 |
| | Muscle | <0.094 | 2.304 | 4.432 | 3.47 | 6.818 | 7.417 | 8.361 | 7.175 |
| | Myocardium | 0.005 | 0.074 | 0.097 | 0.056 | 0.119 | 0.145 | 0.141 | 0.103 |
| | Pancreas | 0.003 | 0.126 | 0.228 | 0.107 | 0.156 | 0.122 | 0.097 | 0.058 |
| | Pituitary gland | n.d. | n.d. | n.d. | n.d. | n.d. | n.d. | n.d. | n.d. |
| | Prostate gland | n.d. | n.d. | n.d. | n.d. | n.d. | n.d. | n.d. | n.d. |
| | Skin | 0.037 | 0.798 | 2.286 | 1.172 | 2.181 | 2.426 | 1.292 | 1.009 |
| | Small intestine mucosa | 0.628 | 6.092 | 5.308 | 0.628 | 0.461 | 0.464 | 0.226 | 0.143 |
| | Spleen | 0.001 | 0.056 | 0.081 | 0.044 | 0.054 | 0.04 | 0.03 | 0.013 |
| | Stomach mucosa | 0.027 | 0.187 | 0.235 | 0.079 | 0.12 | 0.086 | 0.067 | 0.041 |
| | Testis | <0.002 | 0.02 | 0.052 | 0.037 | 0.061 | 0.057 | 0.063 | 0.045 |
| | Thymus | <0.001 | 0.007 | 0.012 | 0.008 | 0.014 | 0.012 | 0.009 | 0.005 |
| | Thyroid gland | <0.001 | 0.001 | 0.002 | 0.001 | 0.001 | 0.001 | 0.001 | <0.001 | n.d. = no data

TABLE 21

| EPA-LPC | | Time after administration (hrs) | | | | | | |
| --- | --- | --- | --- | --- | --- | --- | --- | --- |
| | | 0.5 | 3 | 8 | 24 | 72 | 96 | 168 |
| (% of dose/organ) | Adrenal gland | 0.002 | 0.014 | 0.023 | 0.042 | 0.03 | 0.018 | 0.012 |
| | Blood | 0.44 | 1.89 | 1.16 | 0.542 | 0.342 | 0.374 | 0.238 |
| | Bone | <0.016 | 0.25 | 0.279 | 0.07 | 0.129 | 0.165 | 0.118 |
| | Bone marrow | 0.007 | 0.118 | 0.189 | 0.197 | 0.124 | 0.137 | 0.055 |
| | Brain | 0.001 | 0.031 | 0.023 | 0.052 | 0.152 | 0.27 | 0.251 |
| | Eye (whole) | <0.001 | 0.002 | 0.002 | 0.001 | 0.002 | 0.003 | 0.003 |
| | Fat (white) | 0.017 | 2.92 | 2.36 | 2.68 | 10.7 | 5.01 | 3.94 |
| | Kidney (whole) | 0.034 | 0.237 | 0.307 | 0.344 | 0.304 | 0.242 | 0.19 |
| | Large intestine mucosa | 0.01 | 0.201 | 0.463 | 0.259 | 0.266 | 0.212 | 0.137 |
| | Liver | 0.864 | 13.4 | 12.4 | 8.24 | 5.23 | 4.35 | 2.56 |

TABLE 21-continued

| EPA-LPC | | Time after administration (hrs) | | | | | | |
|---|---|---|---|---|---|---|---|---|
| | | 0.5 | 3 | 8 | 24 | 72 | 96 | 168 |
| | Lung | 0.043 | 0.191 | 0.291 | 0.198 | 0.182 | 0.167 | 0.129 |
| | Muscle | 0.106 | 4.01 | 7.14 | 8.16 | 8.48 | 10.5 | 8.41 |
| | Myocardium | 0.023 | 0.235 | 0.107 | 0.085 | 0.133 | 0.188 | 0.145 |
| | Pancreas | 0.024 | 0.279 | 0.339 | 0.369 | 0.302 | 0.293 | 0.257 |
| | Pituitary gland | <0.001 | 0.001 | <0.001 | 0.001 | 0.001 | 0.001 | 0.002 |
| | Prostate gland | <0.001 | 0.005 | 0.006 | 0.007 | 0.007 | 0.011 | 0.005 |
| | Skin | 0.021 | 1.26 | 1.01 | 0.986 | 1.55 | 1.51 | 1.36 |
| | Small intestine mucosa | 28.4 | 10.2 | 3.13 | 2.23 | 0.861 | 0.542 | 0.389 |
| | Spleen | 0.01 | 0.259 | 0.247 | 0.121 | 0.086 | 0.094 | 0.049 |
| | Stomach mucosa | 0.259 | 0.287 | 0.23 | 0.211 | 0.161 | 0.158 | 0.107 |
| | Testis | <0.002 | 0.04 | 0.054 | 0.077 | 0.069 | 0.093 | 0.081 |
| | Thymus | 0.001 | 0.018 | 0.019 | 0.016 | 0.019 | 0.023 | 0.016 |
| | Thyroid gland | <0.001 | 0.003 | 0.002 | 0.002 | 0.003 | 0.003 | 0.002 |

TABLE 22

| | | Time after administration (hrs) | | | | | | | |
|---|---|---|---|---|---|---|---|---|---|
| | | 0.5 | 3 | 8 | 24 | 72 | 96 | 168 | 336 |
| DHA-PC | Adrenal gland | <0.001 | 0.007 | 0.008 | 0.005 | 0.009 | 0.01 | 0.004 | 0.005 |
| % of dose/tissue | Blood | 0.084 | 0.692 | 0.431 | 0.18 | 0.34 | 0.341 | 0.143 | 0.156 |
| | Bone | <0.017 | 0.202 | 0.305 | 0.068 | 0.166 | 0.331 | 0.134 | 0.0235 |
| | Bone marrow | <0.001 | 0.042 | 0.047 | 0.035 | 0.061 | 0.078 | 0.028 | 0.021 |
| | Brain | <0.001 | 0.015 | 0.02 | 0.027 | 0.134 | 0.176 | 0.109 | 0.228 |
| | Eye (whole) | <0.001 | 0.002 | 0.002 | 0.002 | 0.006 | 0.01 | 0.004 | 0.008 |
| | Fat (white) | 0.052 | 3.976 | 2.57 | 1.892 | 5.701 | 5.942 | 2.365 | 2.691 |
| | Kidney (whole) | 0.011 | 0.156 | 0.154 | 0.091 | 0.205 | 0.287 | 0.101 | 0.091 |
| | Large intestine mucosa | <0.002 | 0.191 | 0.134 | 0.125 | 0.2 | 0.165 | 0.084 | 0.08 |
| | Liver | 0.222 | 7.552 | 5.905 | 2.814 | 3.9 | 3.875 | 1.291 | 1.124 |
| | Lung | 0.007 | 0.113 | 0.076 | 0.046 | 0.096 | 0.108 | 0.047 | 0.04 |
| | Muscle | 0.111 | 6.575 | 6.166 | 2.432 | 8.408 | 14.879 | 5.504 | 10.033 |
| | Myocardium | 0.005 | 0.363 | 0.197 | 0.133 | 0.307 | 0.41 | 0.149 | 0.172 |
| | Pancreas | <0.001 | 0.199 | 0.15 | 0.066 | 0.162 | 0.188 | 0.067 | 0.085 |
| | Pituitary gland | n.d. | n.d. | n.d. | n.d. | n.d. | n.d. | n.d. | n.d. |
| | Prostate gland | n.d. | n.d. | n.d. | n.d. | n.d. | n.d. | n.d. | n.d. |
| | Skin | 0.022 | 0.477 | 0.392 | 0.219 | 1.212 | 2.518 | 0.95 | 1.399 |
| | Small intestine mucosa | 1.801 | 5.223 | 2.541 | 0.492 | 0.545 | 0.612 | 0.23 | 0.19 |
| | Spleen | 0.002 | 0.058 | 0.045 | 0.027 | 0.046 | 0.053 | 0.017 | 0.016 |
| | Stomach mucosa | 0.028 | 0.149 | 0.117 | 0.052 | 0.087 | 0.101 | 0.048 | 0.05 |
| | Testis | <0.002 | 0.016 | 0.018 | 0.025 | 0.082 | 0.083 | 0.047 | 0.069 |
| | Thymus | <0.001 | 0.006 | 0.006 | 0.004 | 0.013 | 0.013 | 0.006 | 0.005 |
| | Thyroid gland | <0.001 | 0.001 | 0.001 | <0.001 | 0.001 | 0.001 | 0.001 | <0.001 | n.d. = no data

TABLE 23

| | | Time after administration (hrs) | | | | | | |
|---|---|---|---|---|---|---|---|---|
| | | 0.5 | 3 | 8 | 24 | 72 | 96 | 168 |
| DHA-LPC | Adrenal gland | 0.003 | 0.014 | 0.026 | 0.011 | 0.015 | 0.035 | 0.012 |
| % of dose/tissue | Blood | 0.421 | 2.1 | 0.674 | 0.315 | 0.358 | 0.364 | 0.202 |
| | Bone | <0.017 | 0.232 | 0.123 | 0.189 | 0.304 | 0.219 | 0.064 |
| | Bone marrow | 0.005 | 0.129 | 0.167 | 0.112 | 0.14 | 0.13 | 0.106 |
| | Brain | 0.001 | 0.027 | 0.058 | 0.077 | 0.247 | 0.333 | 0.441 |
| | Eye (whole) | <0.001 | 0.001 | 0.001 | 0.001 | 0.002 | 0.007 | 0.004 |
| | Fat (white) | <0.017 | 1.49 | 3.8 | 12.2 | 6.59 | 5.57 | 3.79 |
| | Kidney (whole) | 0.022 | 0.27 | 0.433 | 0.337 | 0.396 | 0.422 | 0.181 |
| | Large intestine mucosa | 0.008 | 0.202 | 0.399 | 0.146 | 0.3 | 0.29 | 0.19 |
| | Liver | 1.51 | 19.2 | 15.1 | 11.3 | 7.49 | 6.9 | 2.99 |
| | Lung | 0.034 | 0.23 | 0.157 | 0.166 | 0.143 | 0.164 | 0.114 |
| | Muscle | 0.107 | 4.96 | 12.8 | 8.47 | 14.1 | 21.5 | 16.6 |
| | Myocardium | 0.034 | 0.756 | 0.442 | 0.404 | 0.418 | 0.643 | 0.532 |
| | Pancreas | 0.014 | 0.413 | 0.33 | 0.332 | 0.331 | 0.416 | 0.208 |
| | Pituitary gland | <0.001 | 0.001 | 0.001 | 0.001 | 0.001 | 0.002 | 0.003 |
| | Prostate gland | <0.001 | 0.002 | 0.013 | 0.006 | 0.008 | 0.012 | 0.012 |
| | Skin | 0.042 | 0.512 | 1.09 | 1.17 | 1.52 | 1.75 | 2.1 |
| | Small intestine mucosa | 26 | 4.32 | 5.25 | 2.29 | 1.18 | 0.951 | 0.416 |
| | Spleen | 0.006 | 0.151 | 0.13 | 0.091 | 0.109 | 0.104 | 0.043 |
| | Stomach mucosa | 0.046 | 0.268 | 0.319 | 0.186 | 0.145 | 0.139 | 0.072 |

TABLE 23-continued

| | Time after administration (hrs) | | | | | | |
|---|---|---|---|---|---|---|---|
| | 0.5 | 3 | 8 | 24 | 72 | 96 | 168 |
| Testis | <0.002 | 0.027 | 0.062 | 0.032 | 0.095 | 0.115 | 0.081 |
| Thymus | 0.001 | 0.013 | 0.016 | 0.011 | 0.018 | 0.02 | 0.013 |
| Thyroid gland | <0.001 | 0.002 | 0.002 | 0.002 | 0.002 | 0.003 | 0.001 |

The invention claimed is:

1. A method for making a lysophosphatidylcholine (LPC) composition with a high content of EPA and DHA from a marine raw material containing phospholipids comprising treating the marine raw material with a phospholipase that is not native to the marine raw material to provide a phospholipase treated raw material and fractionating the phospholipase treated raw material to provide an LPC composition characterized in comprising from about 20% to about 100% LPC w/w of the composition and an omega-3 fatty acid content of from 5% to 50% w/w of the composition, a ratio of EPA:DHA of from 1:1 to 3:1 on a w/w basis or a ratio of DHA:EPA of from 1:1 to 5:1 on a w/w basis, and a 2-LPC:1-LPC ratio of from 1:8 to 18:1 on a w/w basis.

2. The method of claim 1 wherein the raw material is selected from the group consisting of a krill lipid preparation, a herring lipid preparation, a herring roe lipid preparation, an algal lipid preparation, and a *Calanus* lipid preparation.

3. The method of claim 2, wherein the krill lipid preparation is a *Euphausia Superba* lipid preparation.

4. The method of claim 1, wherein the raw material is contacted with a phospholipase in a solvent.

5. The method of claim 4, wherein the solvent is a mixture of water and an alcohol.

6. The method of claim 5, wherein the alcohol is ethanol.

7. The method of claim 5, wherein the raw material is contacted with a phospholipase in a mixture of about 85% water and 15% ethanol.

8. The method of claim 1, where the phospholipase is a phospholipase A1 (PLA1).

9. The method of claim 1, wherein the phospholipase is a phospholipase A1 (PLA1) and wherein the enzyme concentration is in the range of 0.1-20 vol/wt %.

10. The method of claim 1, wherein the phospholipase is phospholipase A1 (PLA1) and wherein the method is carried out at a pH of 3-12.

11. The method of claim 1, wherein the phospholipase is phospholipase A1 (PLA1), wherein the method is carried out between 4-95° C.

12. The method of claim 1, wherein the raw material has a content of EPA and DHA in the range of EPA: 1-70 wt % and DHA: 1-70 wt %.

13. The method of claim 1, further comprising the step of concentrating the phospholipase-treated lipid composition to provide a concentrated LPC composition.

14. The method of claim 13, wherein the LPC composition obtained by the process is characterized in comprising from about 40% to about 100% LPC w/w of the composition and an omega-3 fatty acid content of from 5% to 50% w/w of the composition, a ratio of EPA:DHA of from 1:1 to 3:1 on a w/w basis or a ratio of DHA:EPA of from 1:1 to 5:1 on a w/w basis, and a 2-LPC: 1-LPC ratio of from 1:8 to 18:1 on a w/w basis.

15. The method of claim 13, wherein the concentrating step comprises phase separation of the LPC composition with solvents of different polarity to provide a concentrated LPC composition.

16. The method of claim 13, wherein the concentrating step comprises chromatographic separation of the LPC composition to provide a concentrated LPC composition.

17. The method of claim 1, further comprising formulating the LPC composition for human consumption.

* * * * *